United States Patent
Stone et al.

(10) Patent No.: US 11,472,836 B2
(45) Date of Patent: *Oct. 18, 2022

(54) SELECTIVE REMOVAL OF A PROTEIN FROM A MIXTURE OF PROTEINS USING ACTIVATED CARBON BY ADJUSTING SOLUTION CONDITIONS

(71) Applicant: EMD Millipore Corporation, Burlington, MA (US)

(72) Inventors: Matthew T. Stone, Cambridge, MA (US); Mikhail Kozlov, Lexington, MA (US)

(73) Assignee: EMD Millipore Corporation, Burlington, MA (US)

( * ) Notice: Subject to any disclaimer, the term of this patent is extended or adjusted under 35 U.S.C. 154(b) by 448 days.

This patent is subject to a terminal disclaimer.

(21) Appl. No.: 14/768,267

(22) PCT Filed: Feb. 11, 2014

(86) PCT No.: PCT/US2014/015662
§ 371 (c)(1),
(2) Date: Aug. 17, 2015

(87) PCT Pub. No.: WO2014/133741
PCT Pub. Date: Sep. 4, 2014

(65) Prior Publication Data
US 2015/0376232 A1 Dec. 31, 2015

Related U.S. Application Data

(60) Provisional application No. 61/769,269, filed on Feb. 26, 2013.

(51) Int. Cl.
| C07K 1/22 | (2006.01) |
| C07K 1/36 | (2006.01) |
| C07K 16/06 | (2006.01) |

(52) U.S. Cl.
CPC .................. *C07K 1/36* (2013.01); *C07K 1/22* (2013.01); *C07K 16/065* (2013.01); *C07K 2317/14* (2013.01)

(58) Field of Classification Search
None
See application file for complete search history.

(56) References Cited

U.S. PATENT DOCUMENTS

| 4,898,676 A | 2/1990 | Horowitz et al. |
| 5,410,021 A | 4/1995 | Kampen |
| 5,972,225 A | 10/1999 | Karras et al. |
| 6,030,698 A | 2/2000 | Burchell et al. |
| 6,852,224 B2 | 2/2005 | Jagtoyen et al. |
| 7,390,403 B2 | 6/2008 | Siwak |
| 7,712,613 B2 | 5/2010 | Bahm et al. |
| 2003/0038089 A1 | 2/2003 | Levy |
| 2003/0089237 A1 | 5/2003 | Jagtoyen et al. |
| 2003/0104586 A1 | 6/2003 | Abe et al. |
| 2003/0136728 A1 | 7/2003 | Jagtoyen et al. |
| 2005/0205489 A1 | 9/2005 | Siwak |
| 2006/0281075 A1 | 12/2006 | Smith et al. |
| 2008/0105611 A1 | 5/2008 | Collias et al. |
| 2016/0016992 A1* | 1/2016 | Bian ........................ B01J 20/20 |
| | | 530/388.1 |
| 2017/0320909 A1* | 11/2017 | Xenopoulos ......... B01D 15/362 |

FOREIGN PATENT DOCUMENTS

| GB | 2192633 A | 1/1988 | |
| JP | 63-123493 A | 5/1988 | |
| JP | 06-000486 A | 1/1994 | |
| WO | WO-9703092 A1 * | 1/1997 | ............... C07K 1/34 |
| WO | 2000/021591 A1 | 4/2000 | |
| WO | 2000/071467 A1 | 11/2000 | |
| WO | 2005/094605 A1 | 10/2005 | |

OTHER PUBLICATIONS

Lucas, C. et al, "Enzyme linked immunosorbant assays (elisas) for the determination of contaminants resulting from the immuno affinity purification of recombinant proteins." J. Immunol. Meth. (1988) 112(1) p. 113-122).*
Wu, Re-Yong (Amos), "Adsorption of proteins onto activated carbon and phenolic resins." PhD thesis, Purdue University, Dec. 1982.*
Loos, Andreas et al, "Igg-fc glycoengineering in non-mammalian expression hosts." Arch. Biochem. Biophys (May 23, 2012) 526(1) p. 167-173.*
The web page for recrystallization from designer-drug.com, https://www.designer-drug.com/pte/12.162.180.114/dcd/chemistry/equipment/recrystallization.html, available Apr. 1, 2007.*
The Uptima product description sheet for protein A, downloaded Feb. 10, 2020.*
The Agrisera web page discussing IgG, https://www.agrisera.com/en/info/igg.html, downloaded Feb. 10, 2020.*
Lin, Jun et al; "A high resolution capillary isoelectric focusing method for the determination of therapeutic recombinant monoclonal antibody." J. Sep. Sci. (2011) 34 p. 1696-1702.*
International Search Report received for PCT Patent Application No. PCT/US2014/015662, dated May 28, 2014, 3 pages.
Chandy et al., "Evaluation of Heparin Immobilized Chitosan-peg Microbeads for Charcoal Encapsulation and Endotoxin Removal", Artiticial cells, blood substitutes, and immobilization biotechnology, vol. 28, No. 1, Jan. 2000, pp. 65-77.
Chaudhuri et al., "Enteric Virus Removal from Water by Coal-Based Sorbents: Development of Low-Cost Water Filters", Water Science & Technology, vol. 18, No. 10, 1986, pp. 77-82.
Evans et al., "Solute Focusing Techniques for Bioseparations", Biotechnology, vol. 13, No. 1, 1995, pp. 46-52.
Grellet et al., "An Associated Process for the Purification of Immuno Globulin G, Catalase, Superoxide Dismutase and Albumin from Haemolysed Human Placenta Blood", Biotechnology and Applied Biochemistry, vol. 34, 2001, pp. 135-142.

(Continued)

*Primary Examiner* — Fred H Reynolds
(74) *Attorney, Agent, or Firm* — EMD Millipore Corporation

(57) ABSTRACT

The present invention provides novel and improved protein purification processes which incorporate certain types of carbonaceous materials and result in effective and selective removal of certain undesirable impurities without adversely effecting the yield of the desired protein product.

16 Claims, 7 Drawing Sheets

(56) References Cited

OTHER PUBLICATIONS

Guy et al., "The Removal of Virus by a Pilot Treatment Plant", Journal : Water Research, vol. 11, No. 5, 1977, pp. 421-428.
Gyu et al., "Biological Powdered Activated Carbon (BPAC) Microtiltration for Wastewater Reclamation and Reuse Desalination and Water Reuse", International Water Specialists Conference (Perth AUS), Journal: Desalination, vol. 106, No. 1-3, 1996, pp. 39-45.
Heijman et al., "Submicron Powdered Activated Carbon Used as a Pre-coat in Ceramic Micro-filtration", Journal: Desalination and Water Treatment, vol. 9, No. 1-3, 2009, pp. 86-91.
Howell et al., "The in vitro Adsorption of Cytokines by Polymer-pyrolysed Carbon", Biomaterials, vol. 27, No. 30, 2006, pp. 5286-5291.
Kuhn et al., "Purification of Fructooligosaccharides in an Activated Charcoal Fixed Bed Column", Journal: New Biotechnology, vol. 27, No. 6, 2010, pp. 862-869.
Nagaki et al., "Removal of Endotoxin and Cytokines by Adsorbents and the Effect of Plasma-protein Binding", International Journal of Artificial Organs, vol. 14, No. 1, 1991, pp. 43-50.
Pegues et al., "The Removal of 14c Labeled Endotoxin by Activated Charcoal", International Journal of Artificial Organs (ITALY), vol. 2, No. 3, 1979, pp. 153-158.
Powell et al., "Investigating the Effect of Carbon Shape on Virus Adsorption", Environmental Science & Technology, vol. 34 No. 13, 2000, pp. 2779-2783.
Schneiderman et al., "Surface-functionalized Electrospun Carbon Nanofiber Mats as an Innovative Type of Protein Adsorption/purification Medium with High Capacity and High Throughput", Journal of Chromatography A, vol. 1218, Issue 50, Dec. 16, 2011, pp. 8989-8995.
Sridhar, P., "Design of Affinity Membrane Bioseparations", Chemical Engineering & Technology, vol. 19, 1996, pp. 398-404.
Weber et al., "Development of Cationically Modified Cellulose Adsorbents for The Removal of Endotoxins", ASAIO Journal, vol. 41, No. 3, 1995, pp. M430-M434.
Naik et al., "Process for Purification of Monoclonal Antibody Expressed In Transgenic Lemna Plant Extract Using Dextran-Coated Charcoal and Hexamer Peptide Affinity Resin", Journal of Chromatography A, vol. 1260, Aug. 19, 2012, pp. 61-66.
Peng et al., "Selective and Sequential Adsorption of Bovine Serum Albumin and Lysozyme from a Binary Mixture on Nanosized Magnetic Particles", Journal of Colloid and Interface Science, vol. 281, 2005, pp. 11-17.
International Preliminary Report on Patentability received on PCT Patent Application No. PCT/US2014/015662, dated Sep. 11, 2015, 6 pages.

* cited by examiner

SELECTIVE REMOVAL OF A PROTEIN FROM A MIXTURE OF PROTEINS USING ACTIVATED CARBON BY ADJUSTING SOLUTION CONDITIONS

CROSS-REFERENCE TO RELATED APPLICATIONS

The present application is a U.S. National Stage Application of International Application No. PCT/US2014/015662, filing date Feb. 11, 2014, which claims the benefit of priority of U.S. Patent Application No. 61/769,269, filing date Feb. 26, 2013, each of which is incorporated by reference herein in its entirety.

FIELD OF THE INVENTION

The present invention relates to the use of activated carbon to separate a protein from undesirable proteins or proteinaceous impurities by adjusting solution conditions.

BACKGROUND

Activated carbon has previously been used in air filters (see, e.g., U.S. Pat. No. 6,413,303), gas purification (see, e.g., U.S. Pat. No. 7,918,923), decaffeination (see, e.g., U.S. Pat. No. 4,481,223), gold purification (see, e.g., U.S. Pat. No. 5,019,162), fuel purification (see, e.g., U.S. Publication No. 2006/0223705 A1), hemoperfusion (see, e.g., U.S. Pat. No. 4,048,064), treatment of poisonings and overdoses (see, e.g., U.S. Pat. No. 4,453,929), sewage treatment (see, e.g., U.S. Pat. No. 8,329,035), spill cleanup (see, e.g., U.S. Pat. No. 4,770,715), groundwater remediation (see, e.g., U.S. Pat. No. 6,116,816), capture of volatile organic compounds from automobile fuel systems (see, e.g., U.S. Pat. No. 7,044,112), chemical purification (see, e.g., U.S. Pat. No. 4,906,445), distilled alcoholic beverage purification (see, e.g., U.S. Publication No. US 2007/0248730 A1), decolorization of sugar (see, e.g., U.S. Pat. No. 2,082,425), respirators (see, e.g., U.S. Pat. No. 5,714,126), gas masks (see, e.g., U.S. Pat. No. 4,992,084), protective chemical warfare suits (see, e.g., U.S. Pat. No. 7,877,819), and water purification processes (see, e.g., U.S. Pat. No. 7,537,695).

In addition, activated carbon has been used to remove small molecule impurities, such as fatty acids and bilirubin, from serum albumin (see, e.g., Chen et al., J. Biol. Chem., 242: 173-181 (1967); Nakano et al., Anal Biochem., 129; 64-71 (1983); Nikolaev et al., Int. J. Art. Org., 14:179-185 (1991)). Activated carbon has also been used to remove pigments as well as host proteins, proteases, and ribonucleases during the purification of plant viruses (see, e.g., Price, Am. J. Botany, 33: 45-54 (1946); Corbett, Virology, 15:8-15 (1961); McLeana et al., Virology, 31: 585-591 (1967), U.S. Publication No. US 2006/0281075 A1).

Additionally, activated carbon has previously been described as being useful for removal of lower molecular weight plasmid fragments from plasmid DNA. See, Kim et al., J. Biosci. Bioeng. 110:608-613 (2010).

SUMMARY OF THE INVENTION

The present invention is based, at least in part, on the surprising and unexpected discovery that activated carbon can be used for selective removal of a protein from a mixture containing at least two proteins using solution conditions close to the isoelectric point of the protein to be selectively removed.

In some embodiments, a method for selectively removing a protein from a sample comprising at least two proteins is provided, where the method comprises the steps of: (a) providing a sample comprising at least two proteins; (b) adjusting the solution pH of the sample, such that the pH is within 2.0 pH units of the isoelectric point of the protein to be selectively removed; (c) contacting the sample with activated carbon, where the activated carbon binds the protein to be selectively removed; and (d) removing the activated carbon from the sample, thereby resulting in selective removal of the activated carbon bound protein from the sample.

In some embodiments, the solution pH used in a method for selectively removing a protein from a sample, as described herein, is within 1.0 pH unit of the isoelectric point of the protein to be selectively removed.

In some embodiments, a method of increasing the purity of a target protein of interest in a sample comprising the target protein and at least one undesirable protein is provided, where the method comprises the steps of: (a) providing a sample comprising the target protein and at least one undesirable protein; (b) adjusting the solution pH of the sample, such that the pH is within 2.0 pH units of the isoelectric point of the at least one undesirable protein; (c) contacting the sample with activated carbon, where the activated carbon binds at least one undesirable protein; and (d) removing the activated carbon bound to the at least one undesirable protein from the sample, thereby increasing the purity of the target protein in the sample.

In some embodiments, the solution pH used in a method for increasing the purity of a target protein in a sample containing the target protein and at least one undesirable protein, as described herein, is within 1.0 pH unit of the isoelectric protein of the undesirable protein.

In some embodiments, at least one undesirable protein is a proteinaceous impurity.

In some embodiments, the target protein is an immunoglobulin protein such as, an antibody. In some embodiments, the antibody is a monoclonal antibody. In other embodiments, it is a polyclonal antibody.

In some embodiments, the target protein is a non-immunoglobulin protein.

In some embodiments, the sample containing at least two proteins is an aqueous solution derived from a cell culture.

In some embodiments, the cell culture is a Chinese Hamster Ovary (CHO) cell culture.

Other examples of cell culture samples include, but are not limited to HeLa cells, NTH 3T3 cells, BHK cells, VERO cells, CV-1 cells, NS/0 cells, COS cells, baby hamster kidney cells, murine myelomas, hybridoma cells, bacterial cells, yeast cells, insect cells, amphibian cells, human cells, mouse cells, rat cells, dog cells, monkey cells, goat cells, pig cells, cow cells, horse cells, dog cells, cat cells, rabbit cells, bird cells, monkey cells, hamster cells, non-human mammalian cells.

In some embodiments, the protein-containing sample can be the whole cell culture feed. In other embodiments, the cell culture is first clarified and/or purified prior to contacting with activated carbon. Clarification methods include, but are not limited to, centrifugation, settling, depth or screen filtration, complexing with flocculants, and pH change.

In some other embodiments, the sample can be derived from human, animal, or plant tissue or animal fluids, for example, human blood or blood plasma, human tissue, animal blood, goat milk, bovine milk, mammalian milk, animal organs, animal tissue, transgenic animals, transgenic plants, and chicken eggs.

In yet other embodiments, the protein sample is produced by a chemical synthesis from amino acids or smaller peptides.

In some embodiments, the sample is subjected to one or more purification steps or methods prior to subjecting the sample to the methods described herein. Such purification steps or methods include but are not limited to, column and/or membrane chromatography operated in either bind and elute or flow-through mode; crystallization; two- and three-phase partitioning; and filtration.

BRIEF DESCRIPTION OF THE DRAWINGS

As shown in FIG. 6, at pH 4.0, which is far removed from cytochrome C's isoelectric point of pH 10.0-10.5, the activated carbon does not provide efficient removal of the cytochrome C from the solution of cytochrome C and α-lactalbumin. The X-axis depicts the loading of α-lactalbumin in kg/L; the left Y-axis depicts the concentration of cytochrome C in g/L and the right Y-axis depicts the concentration of α-lactalbumin in g/L.

DETAILED DESCRIPTION

Figure 1:
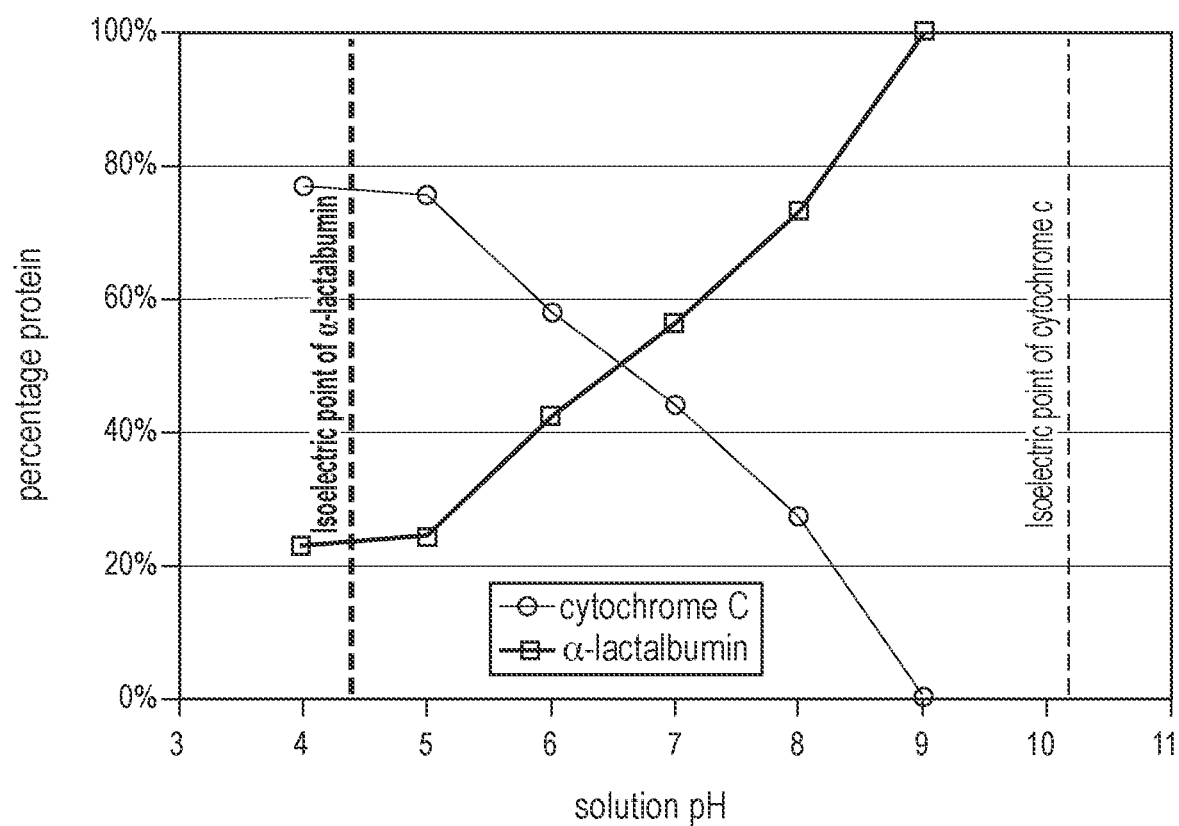
FIG. 1 is a graph depicting the results of a representative experiment to demonstrate the selective removal using activated carbon of cytochrome C from a mixture of cytochrome C and α-lactalbumin (1:1 ratio by weight), when the solution pH is close to the isoelectric point of cytochrome C and, conversely, the selective removal of α-lactalbumin from the mixture when the solution pH is close to the isoelectric point of α-lactalbumin. The X-axis depicts the solution pH and the Y-axis depicts the percentage of the protein in the protein mixture after treatment with activated carbon.

The present invention provides novel and improved processes for selective removal of a protein from a mixture of at least two proteins using activated carbon under solution conditions close to the isoelectric point of the protein to be selectively removed.

Activated carbon has previously been used in water purification processes. In addition, activated carbon has been used to remove small molecule impurities, such as fatty acids and bilirubin, from serum albumin (see, e.g., Chen et al. J. Biol. Chem., 242: 173-181 (1967); Nakano et al., Anal Biochem., 129: 64-71 (1983); Nikolaev et al., Int. J. Art. Org., 14:179-185 (1991)). Activated carbon has also been used to remove pigments as well as host proteins, proteases, and ribonucleases during the purification of plant viruses (see, e.g., Price, Am. J. Botany, 33: 45-54 (1946); Corbett, Virology, 15:8-15 (1961); McLeana et al., Virology, 31: 585-591 (1967).

Further, U.S. patent application Ser. No. 13/565,463, filing date Aug. 2, 2012, incorporated by reference herein in its entirety, describes the use of activated carbon in combination with other media for removal of proteinaceous impurities (e.g., host cell proteins) and DNA from a sample containing a biomolecule of interest (e.g., an antibody).

Accordingly, in general, activated carbon has been reported to non-specifically bind to molecules in solution (e.g., impurities in a water sample).

The present invention is based, at least in part, on the unexpected and surprising finding that activated carbon can be used for selective removal of a protein from a mixture containing two or more proteins by adjusting solution conditions, such that the pH of the solution is close to the isoelectric point of the protein to be selectively removed.

As demonstrated in the Examples herein, activated carbon can be used for selective removal of a protein from a mixture of two or more proteins. Further, as demonstrated in the Examples set forth herein, the degree of removal of the protein can be manipulated by changing pH conditions. Further, activated carbon can be used, as described herein, to increase the purity of a target protein in a solution containing the target protein and one or more undesirable proteins, where the one or more undesirable proteins are selectively removed using activated carbon and the target protein is left behind, thereby increasing the degree of purity of the target protein in the sample.

In some embodiments described herein, activated carbon is used in a flow-through purification mode to selectively remove a protein from a mixture of proteins.

In order that the present disclosure may be more readily understood, certain terms are first defined. Additional definitions are set forth throughout the detailed description.

I. DEFINITIONS

The term "carbonaceous material," as used herein, refers to any substance composed of carbon or containing carbon. In some embodiments, carbonaceous material used in the methods according to the claimed invention is active or activated carbon. In some embodiments, activated carbon comprises activated charcoal. In some embodiments, activated carbon is incorporated into a fibrous media. Fibrous media can be manufactured by a number of methods known in the art, including wet-laying and dry-laying. Fibrous media typically comprises activated carbon, a fiber component, and optionally a binder. Fiber component of the fibrous media can be made from a synthetic material, such as polyamide, polyolefin, polyacrylonitrile, polyester; a natural material, such as cellulose; or a semi-synthetic material, such as a cellulose ester.

The term "active carbon" or "activated carbon," as used interchangeably herein, refers to a carbonaceous material which has been subjected to a process to enhance its pore structure. Activated carbons are porous solids with very high surface areas. They can be derived from a variety of sources including coal, wood, coconut husk, nutshells, and peat. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

Typical activation processes involve subjecting a carbon source, such as, resin wastes, coal, coal coke, petroleum coke, lignites, polymeric materials, and lignocellulosic materials including pulp and paper, residues from pulp production, wood (like wood chips, sawdust, and wood flour), nut shell (like almond shell and coconut shell), kernel, and fruit pits (like olive and cherry stones) to a thermal process (e.g., with an oxidizing gas) or a chemical process (e.g., with phosphoric acid or metal salts, such as zinc chloride). An exemplary process involving chemical activation of wood-based carbon with phosphoric acid ($H_3PO_4$) is disclosed in U.S. Pat. No. Re. 31,093, which resulted in an improvement in the carbon's decolorizing and gas adsorbing abilities. Also, U.S. Pat. No. 5,162,286 teaches phosphoric acid activation of wood-based material which is particularly dense and which contains a relatively high (30%) lignin content, such as nut shell, fruit stone, and kernel. Phosphoric acid activation of lignocellulose material is also discussed in U.S. Pat. No. 5,204,310, as a step in preparing carbons of high activity and high density. The teachings of each of the patents listed in this paragraph are incorporated by reference herein in their entirety.

In contrast to most other adsorbing materials, activated carbon is believed to interact with molecules using relatively weak Van der Waals or London dispersion forces. Typical commercial activated carbon products exhibit a surface area of at least 300 $m^2/g$, as measured by the nitrogen adsorption based Brunauer-Emmett-Teller ("BET") method, which is method well known in the art.

Although, active or activated carbon has been previously employed in processes for purifying liquids and gases as well as for purifying a recombinantly expressed antibody from other impurities by binding to impurities, it has not been previously employed for selectively removing a protein from a mixture of two or more proteins by employing solution conditions based on the properties of the protein to be selectively removed. Consequently, by selectively removing a protein from a mixture of two or more proteins, the purity of the proteins that are not removed is increased.

In some embodiments, the mixture of two or more proteins includes at least one protein which is to be selectively removed and another protein which is to be purified using the methods described herein. In general, the purity of the protein which remains after the selective removal of one or more other proteins in the mixture increases, following the selective removal of other proteins. The protein whose purity is increased is referred to as the target protein. The target protein may be an immunoglobulin or a non-immunoglobulin protein. In some embodiments, the target protein is an immunoglobulin protein, e.g., a monoclonal antibody.

The following are examples of proteins that can be purified according to the present invention. As discussed above, in some embodiments, the target protein is a monoclonal antibody. Other examples of target proteins include recombinant proteins which include, but are not limited to, recombinant human growth hormone, recombinant human insulin, recombinant follicle-stimulating hormone, recombinant factor VII (anti-hemophilic factor), recombinant human erythropoietin, recombinant granulocyte colony-stimulating factor, recombinant alpha-galactosidase a, recombinant iduronidase, recombinant galsulfase, recombinant dornase alfa, recombinant tissue plasminogen activator, recombinant human interferons, recombinant insulin-like growth factor 1, and recombinant asparaginase.

In other embodiments of this invention, target proteins are proteins derived from human blood or other physiological fluids. Examples of such proteins include, but not limited to, immunoglobulins G and M, Factor VIII, Factor IX, anti-thrombin III, and alpha-I-antitrypsin.

The term "immunoglobulin," "Ig" or "IgG" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies).

The term "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $CH_2$/$CH_3$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

As discussed above, in some embodiments, a target protein is an Fc region containing protein, e.g., an immunoglobulin. In some embodiments, an Fc region containing protein is a recombinant protein which includes the Fc region of an immunoglobulin fused to another polypeptide or a fragment thereof.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal.

The term "monoclonal antibody" or "Mab," as used interchangeably herein, refers to an antibody obtained from a population of substantially homogeneous antibodies, i.e., the individual antibodies in the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991).

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, $5^{th}$ Ed. Public Health Service. National Institutes of Health, Bethesda. Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain. Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593- 596 (1992).

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "solution," "composition" or "sample," as used herein, refers to a mixture of two or more proteins, where one of the proteins is a target protein or protein of interest to be purified and the other one or more proteins are undesirable and are selectively removed using methods described herein. In some embodiments, the sample comprises cell culture feed, for example, feed from a mammalian cell culture (e.g., CHO cells) containing two or more proteins. However, samples also encompass non-mammalian expression systems used for producing a protein of interest or target protein.

The term "non-mammalian expression systems," as used herein, refers to all host cells or organisms employed to generate therapeutic proteins, where the host cells or organisms are of non-mammalian origin. Examples of non-mammalian expression systems used for producing a protein of interest or target protein include yeast such as, *Saccharomyces cerevisiae* and *Pichia pastoris*, bacteria such as *Escherichia coli, Bacillus megaterium, Brevibacillus choshinensis*, insect cells such as *Spodoptera frugiperda* cells. Baculovirus infected insect cells, and algae cells.

As used herein, the term "polypeptide" generally refers to peptides and proteins having more than about ten amino acids. The terms "protein of interest" and "target protein," as used interchangeably herein, refer to a protein or polypeptide, which is to be purified from a mixture of two or more proteins or polypeptides, by selective removal of the other proteins or polypeptides in the mixture.

The terms "purifying," "increasing the purity," "separating," or "isolating," as used interchangeably herein, refer to increasing the ratio of target protein to one or more other proteins in a mixture by selectively removing the one or more other proteins from the mixture using the methods described herein. Typically, the purity of the target protein is increased by 50%, or by 60%, or by 70%, or by 80%/o, or by 90% or more, following removal of one or more other proteins present in the sample containing the target protein.

As used interchangeably herein, the terms "selectively removing" and "selective removal" refer to removing a protein from a mixture of two or more proteins by exposing the mixture to a carbonaceous material (e.g., activated carbon) under pH conditions, which are within about 2.0 pH units of the isoelectric point of the protein which is removed. Accordingly, in various embodiments described herein, activated carbon is added to a mixture of two or more proteins under pH conditions which are close to the isoelectric point of a protein desired to be removed, thereby resulting in activated carbon to bind to the protein. The activated carbon is subsequently removed from the mixture, thereby resulting in the removal of the bound protein.

The terms "flow-through process," "flow-through mode," and "flow-through chromatography," as used interchangeably herein, refer to a product separation technique in which at least one product in a sample is intended to flow through a carbonaceous media, while at least one potential component binds to the carbonaceous media (e.g., activated carbon).

The sample intended to flow through is generally referred to as the "mobile phase." The "flow-through mode" is generally an isocratic operation (i.e., a process during which the composition of the mobile phase is not changed). The media used for flow-through is usually pre-equilibrated with the same buffer solution that contains the target protein molecule. After purification, the media can be flushed with additional quantity of the same buffer to increase the product recovery.

The term "buffer" refers to a solution that resists changes in pH by the action of its acid-base conjugate components. Various buffers which can be employed in the methods described herein are described in Buffers. A Guide for the Preparation and Use of Buffers in Biological Systems. Gueffroy, D., ed. Calbiochem Corporation (1975). Different buffers maintain different ranges of pH, for example phosphate buffer is usually used for pH between 6.0 and 8.0, while for a higher pH, a borate buffer can be used, and for lower pH, a carbonate buffer can be used. Persons of ordinary skill in the art will be able to readily identify a suitable buffer to use, depending on the pH to be maintained. Non-limiting examples of buffers that can be used in the methods according to the present invention include MES, MOPS, MOPSO, Tris, HEPES, phosphate, acetate, citrate, succinate, carbonate, borate, and ammonium buffers, as well as combinations of these.

The term "wash buffer" or "equilibration buffer" are used interchangeably herein, refers to a buffer used to wash or re-equilibrate the carbonaceous material prior to contacting a mixture of proteins with the carbonaceous material.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

The "pI" or "isoelectric point" of a polypeptide refers to the pH at which the polypeptide's positive charge balances its negative charge. pI can be calculated from the net charge of the amino acid residues or sialic acid residues of attached carbohydrates of the polypeptide or can be determined using one or more of the following methods that are well known in the art: isoelectric focusing electrophoresis gel; capillary isoelectric focusing electrophoresis; chromatofocusing; isoelectric precipitation; and ion-exchange chromatography.

II. EXEMPLARY CARBONACEOUS MATERIALS FOR USE IN THE METHODS DESCRIBED HEREIN

In methods according to the present invention, certain carbonaceous materials such as, activated carbon, are used for selective removal of proteins. Activated carbon can be described as a porous solid with a very high surface area. In some embodiments, activated carbon comprises activated charcoal. Activated carbon can be derived from a variety of sources including, but not limited to, coal, wood, coconut husk, nutshells, and peat. Activated carbon can be produced from these materials by physical activation involving heat under a controlled atmosphere or by chemical activation using strong acids, bases, or oxidants. The activation processes produce a porous structure with a high surface area that gives activated carbon a greater capacity for impurity removal. Activation processes can be modified to control the acidity of the surface.

Activated carbon is available from a wide variety of commercial sources and comes in a number of grades and formats. Some of the commercial suppliers of activated carbon include companies such as MeadWestVaco Corp., Richmond, Va., USA; Norit Americas Inc., Marshall, Tex., USA; Calgon Carbon Corp., Pittsburgh, Pa., USA.

In some embodiments described herein, activated carbon is incorporated in a cellulose-containing fibrous media, as described herein.

Commercially available activated carbon materials that may be employed in the methods according to the present invention include, but are not limited to, Nuchar HD activated carbon (MeadWestVaco Corporation, Richmond, Va., USA); Nuchar SA 20 (MeadWestVaco Corporation, Richmond, Va., USA); Nuchar SN (MeadWestVaco Corporation. Richmond, Va., USA); Nuchar WV-B 30 (MeadWestVaco Corporation, Richmond, Va., USA); RGC Powder activated carbon (MeadWestVaco Corporation, Richmond, Va., USA); Norit Darco KB-G activated carbon (Norit Americas Inc., Marshall, Tex., USA); Norit CGP Super activated carbon (Norit Americas Inc., Marshall, Tex., USA); Norit A Supra USP (Norit Americas Inc., Marshall, Tex., USA); Norit E Supra USP (Norit Americas Inc., Marshall, Tex., USA); Norit C GRAN (Norit Americas Inc., Marshall, Tex., USA); Norit SX Ultra (Norit Americas Inc., Marshall, Tex., USA); and Chemviron Pulsorb PGC activated carbon (Chemviron Carbon, Feluy, Belgium).

Two major formats of activated carbon are powdered and granular. Powdered activated carbon contains small and usually less than 1 mm diameter particles, and is most commonly used for purification of liquids. Granular activated carbon has a larger particle size and consequently a smaller surface area, so it is preferred for use in gas purification where the rate of diffusion is faster.

An important consideration for safety with use of activated carbon in consumer applications (such as water, food, beverage, and pharmaceutical purification) is reduction and control of extractable compounds. Activated carbon intended for drinking water and food contact applications is usually made in compliance with safety standard ANSI/NSF Standard 61 that covers all indirect additives to water. Also, ASTM standard test method D6385 describes determining acid extractable content in activated carbon by ashing and could be used to study and minimize the level of extractables from activated carbon.

A range of activated carbon types is available for various applications. For example, MeadWestVaco Corp. supplies at least twelve types of powdered activated carbon that vary by their capacity, surface acidity, pore accessibility to target molecules, and intended application. It is generally desirable to maximize the capacity of activated carbon for impurity removal.

In some embodiments described herein, activated carbon is incorporated in a cellulose media.

III. USE OF CARBONACEOUS MATERIAL IN PURIFICATION PROCESSES

One general procedure which may be used for selectively removing a protein from a solution containing at least two proteins is described below.

In some embodiments, the protein to be selectively removed using the methods described herein is an undesirable protein or proteinaceous impurity, which may be removed by static treatment of the mixture with activated carbon. The pH of a solution containing at least two proteins is adjusted to a pH which is within 2.0 pH units or 1.0 pH unit of the isoelectric point of the protein or proteinaceous impurity to be selectively removed. The pH can be adjusted by the addition of acid or base to the solution. The solution pH can also be adjusted by dilution of the solution with a buffer having the desired solution pH or by dialysis or diafiltration of the solution into a buffer having the desired solution pH. Activated carbon is subsequently added to the pH adjusted solution either in dry form or suspended in an aqueous solution. The solution is then allowed to interact with the activated carbon for a period of time up to 48 hours. The activated carbon is preferably kept suspended within the solution in order to maximize the rate of protein impurity adsorption. The solution can be agitated by movement of the solution container or stirring the solution with a magnetic stir bar or stirring the solution with a mechanical agitator.

The activated carbon is then separated out from the solution, where the activated carbon is bound to the protein to be selectively removed. The bound activated carbon can be separated by filtering the solution and recovering the solution filtrate. Alternatively, the bound activated carbon can be separated by centrifuging the solution or allowing the bound activated carbon to settle and recovering the supernatant solution. If any fine particles remain in the supernatant after centrifugation or settling, they can be removed by filtration. The remaining solution contains reduced levels of the protein which is selectively removed.

In another embodiment, the following procedure maybe used to selectively remove a protein from a solution containing at least two proteins.

The pH of a solution containing at least two proteins is adjusted to a pH which is within 2.0 pH units or within 1.0 pH unit of the isoelectric point of the protein which is desired to be selectively removed. The pH may be adjusted by the addition of an acid or a base to the solution. The solution pH can also be adjusted by dilution of the solution with a buffer having the desired pH. Further, the solution pH can be adjusted by dialysis or diafiltration of the solution into a buffer having the desired pH.

In some embodiments, a chromatography device, e.g., a column, is loaded with an aqueous slurry of activated carbon. Activated carbon can also be loaded into a device, e.g., a column, as a dry powder and then wetted with an aqueous solution. However, sometimes it may be challenging to remove small air bubbles from in between the activated carbon particles when the column is dry packed. The column is then equilibrated with a buffer having the same pH as the solution containing the proteins. Then the solution is subsequently passed through the activated carbon column at a flow-rate that results in a column residence time of between 15 secs and 10.0 mins. The eluate from the column is then collected which does not contain or contains reduced levels of the protein that was selectively removed using the activated carbon.

In various embodiments, the activated carbon which is bound to the protein to be selectively removed may be removed from the sample containing the target protein by filtration or centrifugation or a combination of both centrifugation and filtration.

When starting with a mixture of proteins, the isoelectric point of all the proteins in the mixture can be readily determined by subjecting the mixture to isoelectric focusing electrophoresis gel or capillary isoelectric focusing. Further resolution of complex mixtures may be achieved by analysis by two-dimensional gel electrophoresis that separates the proteins by both their isoelectric point and then their size. Based on this information, solution conditions can be adjusted when using activated carbon to remove proteins other than the target protein, as described herein.

This invention is further illustrated by the following examples which should not be construed as limiting. The contents of all references, patents and published patent applications cited throughout this application, as well as the Figures, are incorporated herein by reference.

EXAMPLES

Example 1

Exploiting Solution pH to Selectively Remove Either Cytochrome C or α-Lactalbumin from a 1-to-1 by Weight Solution with Activated Carbon This representative example demonstrates that a protein can be selectively removed from a mixture of two proteins, initially present in equal concentrations in the mixture, using activated carbon by manipulating the pH of the starting solution. In this experiment, selective removal of either cytochrome C or α-lactalbumin was obtained with activated carbon using a solution pH in the vicinity of the isoelectric point of the protein desired to be selectively removed.

A 1-to-1 by weight solution of cytochrome C and α-lactalbumin was treated with activated carbon at pH 4.0, 5.0, 6.0, 7.0, 8.0 and 9.0 under static conditions, as described below.

A 1-to-1 by weight of protein stock solution was prepared by dissolving 200 mg of α-lactalbumin from bovine milk (≥85% by PAGE, product number L5385, lot number 110M7003V, Sigma-Aldrich Corporation, St. Louis, Mo., 63103, USA) and 200 mg of cytochrome C from equine heart (≥95% by SDS-PAGE, product number C2506, lot number 041M7008V, Sigma-Aldrich Corporation, St. Louis, Mo., 63103, USA) in 100 mL water. The stock solution was then filtered through a 0.22 μm membrane (Stericup-GP 0.22 μm Millipore Express PLUS membrane, 250 mL, catalogue number: SCGPU02RE, EMD Millipore Corporation, Billerica, Mass., 01821. USA).

Three 15 mL centrifuge tubes for each of pH 4.0, 5.0, 6.0, 7.0, 8.0, and 9.0, were loaded with 10 mg of Nuchar HD activated carbon (MeadWestVaco Corporation, Richmond, Va., USA). Three separate 15 mL centrifuge tubes for each of pH 4.0, 5.0, 6.0, 7.0, 8.0, and 9.0 were used as controls with no activated carbon. Then 2.5 mL of buffer at the appropriate pH (50 mM acetate for pH 4.0, 5.0, 6.0 or 50 mM Tris for pH 7.0, 8.0, 9.0) was added to each tube. Then 2.5 mL of the 1-to-1 protein stock solution containing 2.0 mg/mL of α-lactalbumin and 2.0 mg/mL of cytochrome C was added to each tube. The resulting solutions had 1.0 mg/mL of α-lactalbumin and 1.0 mg/mL of cytochrome C. The tubes were allowed to rotate for 20 hours.

The tubes were subsequently subjected to centrifugation and the supernatant solutions were filtered through a 0.22 micron membrane (Millex-CGV 0.22 micron Filter Unit Durapore PVDF Membrane, EMD Millipore Corporation, Billerica, Mass., 01821, USA) in order to remove any activated carbon particles that might remain suspended in solution. The samples were analyzed by reverse phase HPLC (Instrument: Agilent 1290 UPLC. Column: Higgins Analytical Targa C18, Mobile phase: Solvent A—0.1% trifluoroacetic acid in MilliQ Water, Solvent B—0.1% trifluoroacetic acid in 100% acetonitrile (HPLC grade), Flow rate: 1 ml/min, gradient: 0-15 min, 5%-95% B, with 10 minute post-time to re-equilibrate column, wavelength of UV detector: 230 nm (550 nm reference, temperature: 25° C.). The recovery of the proteins was calculated based on the areas measured in the HPLC peaks.

As summarized in Table I below and depicted in FIG. 1, this experiment demonstrates that it is possible to selectively remove a single protein from a solution composed of two proteins with different isoelectric points by adjusting the solution pH such that it is close to the isoelectric point of the protein to be removed. For example, following the treatment of the 1-to-1 by weight protein solution with activated carbon at pH 4.0, which happens to be close to the isoelectric point of α-lactalbumin, the composition of cytochrome C in the solution is enriched from 50% to 77%, while the composition of α-lactalbumin in solution was reduced from 50% to 23%.

Conversely, treatment of the 1-to-1 by weight protein solution with activated carbon at pH 9.0, which happens to be close to the isoelectric point of cytochrome C, enriches the solution composition of α-lactalbumin from 50% to 100%, while the solution composition of cytochrome C is reduced from 50° % to 0%.

FIG. 1 depicts the percentage composition of cytochrome C and α-lactalbumin in solutions composed of 1.0 mg/mL cytochrome C and 1.0 mg/mL of α-lactalbumin (50%:50% ratio) following treatment with activated carbon at pH 4.0, 5.0, 6.0, 7.0, 8.0, and 9.0 under static conditions. As shown, activated carbon selectively removes the cytochrome C when the solution pH is close to its isoelectric point of 10.0-10.5 and selectively removes the α-lactalbumin when the solution pH is close to its isoelectric point of 4.8. The graph indicates the unexpected result that activated carbon can be used to selectively remove a protein when the solution pH is close to the isoelectric point of the protein to be removed.

TABLE I

The recovery of cytochrome C, the recovery of α-lactalbumin, and the ratio of cytochrome C to α-lactalbumin after solutions composed of 1.0 mg/mL cytochrome C and 1.0 mg/mL of α-lactalbumin (50%:50% ratio) were treated with activated carbon at pH 4.0, 5.0, 6.0, 7.0, 8.0, or 9.0 under static conditions.

| pH | cytochrome C recovery | α-lactalbumin recovery | ratio of cytochrome C:α-lactalbumin |
|---|---|---|---|
| 4 | 94% | 28% | 77%:23% |
| 5 | 82% | 26% | 76%:24% |
| 6 | 63% | 46% | 58%:42% |
| 7 | 46% | 58% | 44%:56% |
| 8 | 26% | 69% | 27%:73% |
| 9 | 0% | 77% | 0%:100% |

Example 2

Selective Removal of Cytochrome C from a Solution Containing Both Cytochrome C and α-Lactalbumin This representative example demonstrates that an undesirable protein or a model proteinaceous impurity can be selectively removed from a solution containing a target protein using activated carbon, when the pH of the starting solution is manipulated such that it is close to the isoelectric point of the undesirable protein or model proteinaceous impurity. In this experiment, a solution of α-lactalbumin containing 100,000 ppm of cytochrome C, which may be analogous to the levels of many proteinaceous impurities, was treated with activated carbon at pH 4.0 or 9.0 under static conditions to demonstrate that cytochrome C can be selectively and efficiently removed with activated carbon by choosing a solution pH close to the isoelectric point of cytochrome C.

A solution was prepared from 400 mg of α-lactalbumin from bovine milk (≥85% by PAGE, product number L5385, lot number 110M7003V, Sigma-Aldrich Corporation, St. Louis, Mo., 63103, USA), 40 mg of cytochrome C from equine heart (≥95% by SDS-PAGE, product number C2506, lot number 84H7135 Sigma-Aldrich Corporation, St. Louis, Mo., 63103, USA) and 40 mL of water. The protein stock solution was then filtered through a 0.22 µm membrane (Stericup-GP 0.22 µm Millipore Express PLUS membrane, 250 mL, catalogue number: SCGPU02RE, EMD Millipore Corporation, Billerica, Mass., 01821, USA).

Three 15 mL centrifuge tubes for pH 4.0 and pH 9.0 were loaded with 10 mg of Nuchar HD activated carbon (MeadWestVaco Corporation, Richmond, Va., USA). Three separate 15 mL centrifuge tubes at pH 4.0 and pH 9.0 were used as controls with no activated carbon. Then 2.5 mL of buffer at the appropriate pH (50 mM acetate or pH 4.0, 50 mM Tris for pH 9.0) was added to each tube. Subsequently, 2.5 mL of the stock protein solution having 10.0 mg/mL of α-lactalbumin and 1.0 mg/mL of cytochrome C in water was added to each tube. This resulted in a solution with 5.0 mg/mL of α-lactalbumin, 0.5 mg/mL of cytochrome C, and a buffer concentration of 25 mM. The tubes were allowed to rotate for 20 hours.

The tubes were subsequently subjected to centrifugation and the supernatant solutions were filtered through a 0.22 micron membrane (Millex-GV 0.22 micron Filter Unit Durapore PVDF Membrane, EMD Millipore Corporation, Billerica, Mass., 01821, USA) in order to remove any activated carbon particles that might remain suspended in solution. The samples were analyzed by reverse phase HPLC (Instrument: Agilent 1290 UPLC, Column: Higgins Analytical Targa C18, Mobile phase: Solvent A—0.1% trifluoroacetic acid in MilliQ Water, Solvent B—0.1% trifluoroacetic acid in 100% acetonitrile (HPLC grade), flow rate: 1 ml/min, gradient: 0-15 min, 5%-95% B, with 10 minute post-time to re-equilibrate column, wavelength of UV detector: 230 nm (550 nm reference, temperature: 25° C.). The recovery of the proteins was calculated based on the areas measured in the HPLC peaks.

As demonstrated by the results in Table II, cytochrome C, used as a model proteinaceous impurity, was selectively and efficiently removed from the solution containing cytochrome C and α-lactalbumin at pH 9.0, which is near the isoelectric point of cytochrome C (pI 10.0-10.5). In contrast, very little of the cytochrome C is removed from the solution at pH 4.0, which is further away from the isoelectric point of cytochrome C.

Accordingly, a similar separation could be performed to remove any proteinaceous impurity which may be present in a solution containing a target protein of interest, by adding activated carbon to the solution having a pH which is close to the isoelectric point of the proteinaceous impurity.

TABLE II

The recovery of α-lactalbumin, the concentration of cytochrome C, and the LRV of cytochrome C removed after solutions composed of 5.0 mg/mL of α-lactalbumin and 0.5 mg/mL of cytochrome C (100,000 ppm) were treated with activated carbon at pH 4.0 or pH 9.0.

| pH | α-lactalbumin recovery | cyctochrome C concentration (ppm) | log reduction value of cytochrome C |
|---|---|---|---|
| 4 | 84% | 113,420 | −0.05 |
| 9 | 93% | 13,794 | 0.86 |

Example 3

Selective Removal of α-Lactalbumin Protein from a Solution of Cytochrome C

This representative example further demonstrates that yet another undesirable protein or model proteinaceous impurity can be selectively removed from a solution containing target protein using activated carbon when the pH of the starting solution is brought close to the isoelectric point of the undesirable protein or model proteinaceous impurity. In contrast to Example 2, the model impurity to be removed here is α-lactalbumin. In this experiment, a solution of cytochrome C with 100,000 ppm of α-lactalbumin was treated with activated carbon at pH 4.0 or 9.0 under static conditions to demonstrate that α-lactalbumin can also be selectively and efficiently removed with activated carbon by choosing a solution pH close to the isoelectric point of the α-lactalbumin protein.

A solution was prepared from 400 mg of cytochrome C from equine heart (≥95% by SDS-PAGE, product number C2506, lot number 84117135 Sigma-Aldrich Corporation, St. Louis, Mo., 63103, USA), 40 mg of α-lactalbumin from bovine milk (≥85% by PAGE, product number 1.5385, lot number 110M7003V, Sigma-Aldrich Corporation, St. Louis, Mo., 63103, USA) and 40 mL of water. The protein stock solution was then filtered through a 0.22 µm membrane (Stericup-GP 0.22 µm Millipore Express PLUS membrane, 250 mL, catalogue number: SCGPU02RE, EMD Millipore Corporation. Billerica, Mass., 01821, USA).

Three 15 mL centrifuge tubes for pH 4.0 and pH 9.0 were loaded with 10 mg of Nuchar HD activated carbon (MeadWestVaco Corporation, Richmond, Va., USA). Three separate 15 mL centrifuge tubes for pH 4.0 and pH 9.0 were used as controls with no activated carbon. Subsequently, 2.5 mL of buffer at the appropriate pH (50 mM acetate for pH 4.0, 50 mM Tris for pH 9.0) was added to each tube. This was followed by the addition of 2.5 mL of the stock protein solution having 10.0 mg/mL of cytochrome C and 1.0 mg/mL of α-lactalbumin in water to each tube, which resulted in a solution with 5.0 mg/mL of cytochrome C, 0.5 mg/mL of α-lactalbumin, and a buffer concentration of 25 mM. The tubes were allowed to rotate for 20 hours.

The tubes were subjected to centrifugation and the supernatant solutions were filtered through a 0.22 micron membrane (Millex-GV 0.22 micron Filter Unit Durapore PVDF Membrane, EMD Millipore Corporation, Billerica, Mass., 01821, USA) in order to remove any activated carbon particles that might remain suspended in solution. The samples were analyzed by reverse phase HPLC (Instrument: Agilent 1290 UPLC, Column: Higgins Analytical Targa C18, Mobile phase: Solvent A—0.1% trifluoroacetic acid in MilliQ Water, Solvent B—0.1% trifluoroacetic acid in 100% acetonitrile (HPLC grade), flow rate: 1 ml/min, gradient: 0-15 min. 5%-95% B, with 10 minute post-time to re-equilibrate column, wavelength of UV detector: 230 nm (550 nm reference, temperature: 25° C.). The recovery of the proteins was calculated based on the areas measured in the HPLC peaks.

As demonstrated in Table III, the α-lactalbumin protein was selectively and efficiently removed from the solution containing both cytochrome C and α-lactalbumin at pH 4.0, which is near the isoelectric point of α-lactalbumin (pI 4.8). In contrast, very little of the α-lactalbumin protein is removed at pH 9.0, which is further away from the isoelectric point of α-lactalbumin.

Accordingly, both Examples 2 and 3 further confirmed that a protein can be selectively and efficiently removed from a solution using activated carbon, if the pH of the solution is close to the isoelectric point of the protein which is to be removed using activated carbon. This finding is both novel and unexpected and may be used in many different instances, where it is desirable to remove a specific protein from a solution or to remove a protein from a mixture of proteins.

TABLE III

The recovery of cytochrome C, the concentration of α-lactalbumin, and the LRV of α-lactalbumin removed after solutions composed of 5.0 mg/mL cytochrome C and 0.5 mg/mL of α-lactalbumin (100,000 ppm) were treated with activated carbon at pH 4.0 or pH 9.0.

| pH | cytochrome C recovery | α-lactalbumin concentration (ppm) | log reduction value of α-lactalbumin |
|---|---|---|---|
| 4 | 95% | 5,873 | 1.23 |
| 9 | 82% | 88,968 | 0.05 |

Example 4

Optimal Solution pH for the Removal of a Protein from a Mixture Containing a Monoclonal Antibody This representative example demonstrates that a model proteinaceous impurity can be selectively removed from a solution containing a monoclonal antibody as the target protein, using activated carbon, when the pH of the starting solution is brought close to the isoelectric point of the impurity. A solution containing MAb I monoclonal antibody and 200,000 ppm cytochrome C was treated with activated carbon at pH 4.0, 5.0, 6.0, 7.0, 8.0 and 9.0 under static conditions to demonstrate that cytochrome C can be selectively and efficiently removed from the solution using activated carbon when the solution pH is close to cytochrome C's isoelectric point.

A 10.0 mg/mL solution of MAb I monoclonal antibody was dialyzed into water to remove buffer salts with dialysis tubing (Standard RC Dialysis Trial Kits, Spectra/Por® 1-3, 3.5K MWCO, 54 mm FLAT WIDTH, serial number: 132725, Spectrum Laboratories, Inc. Rancho Dominguez, Calif., 90220 USA). A portion of the dialyzed MAB I solution was then concentrated using Amicon Ultra-15 Centrifugal Filter Units (3 kDa, catalogue Number: UFC900324, EMD Millipore Corporation, Billerica, Mass., 01821, USA). The concentrated portion of the solution was recombined with the rest of the dialyzed MAB 1 solution to give stock solution with a concentration of 10.0 mg/mL. The MAB I stock solution was then filtered through a 0.22 µm membrane (Stericup-GP 0.22 µm Millipore Express PLUS membrane, 250 mL, catalogue number: SCGPU02RE, EMD Millipore Corporation, Billerica, Mass., 01821, USA).

200 mg of cytochrome C from equine heart (≥95% by SDS-PAGE, product number C2506, lot number 041M7008V, Sigma-Aldrich Corporation, St. Louis, Mo., 63103, USA) was dissolved into 100 mL of the 10.0 mg/mL MAB I solution. The stock solution was filtered through a 0.22 µm membrane (Stericup-GP 0.22 µm Millipore Express PLUS membrane, 250 mL, catalogue number SCOGPU02RE, EMD Millipore Corporation, Billerica, Mass., 01821, USA).

Three 15 mL centrifuge tubes for pH 4.0, 5.0, 6.0, 7.0, 8.0, and 9.0 were loaded with 10 mg of Nuchar HD activated carbon (MeadWestVaco Corporation, Richmond, Va., USA). Three separate 15 mL centrifuge tubes for pH 4.0, 5.0, 6.0, 7.0, 8.0, and 9.0 were used as controls with no activated carbon. 2.5 mL of buffer at the appropriate pH (50 mM acetate for pH 4.0, 5.0, 6.0 or 50 mM Tris for pH 7.0, 8.0, 9.0) was added to each tube. 2.5 mL of the stock solution containing 10.0 mg/mL of MAB I and 2 mg/mL of cytochrome C was added to each tube. The resulting solutions had 5.0 mg/mL of MAB I, 1.0 mg/mL of cytochrome C, and a buffer concentration of 25 mM. The tubes were allowed to rotate for 20 hours.

The tubes were subsequently subjected to centrifugation and the supernatant solutions were filtered through a 0.22 micron membrane (Millex-GV 0.22 micron Filter Unit Durapore PVDF Membrane. EMD Millipore Corporation, Billerica, Mass., 01821, USA) in order to remove any activated carbon particles that might remain suspended in solution. The samples were analyzed by analytical size-exclusion chromatography (Instrument: Agilent 1260 HPLC; Column: Tosoh BiosciencesTSK-Gel Super SW3000; Mobile phase: 0.2M sodium phosphate pH 7.0; flow rate: 0.35 ml/min, isocratic gradient, 15 min run time; wavelength of UV detector: 230 nm; temperature: 25 degree C.). The recovery of each protein was calculated based on the A230 areas measured in the HPLC peaks.

Figure 2:
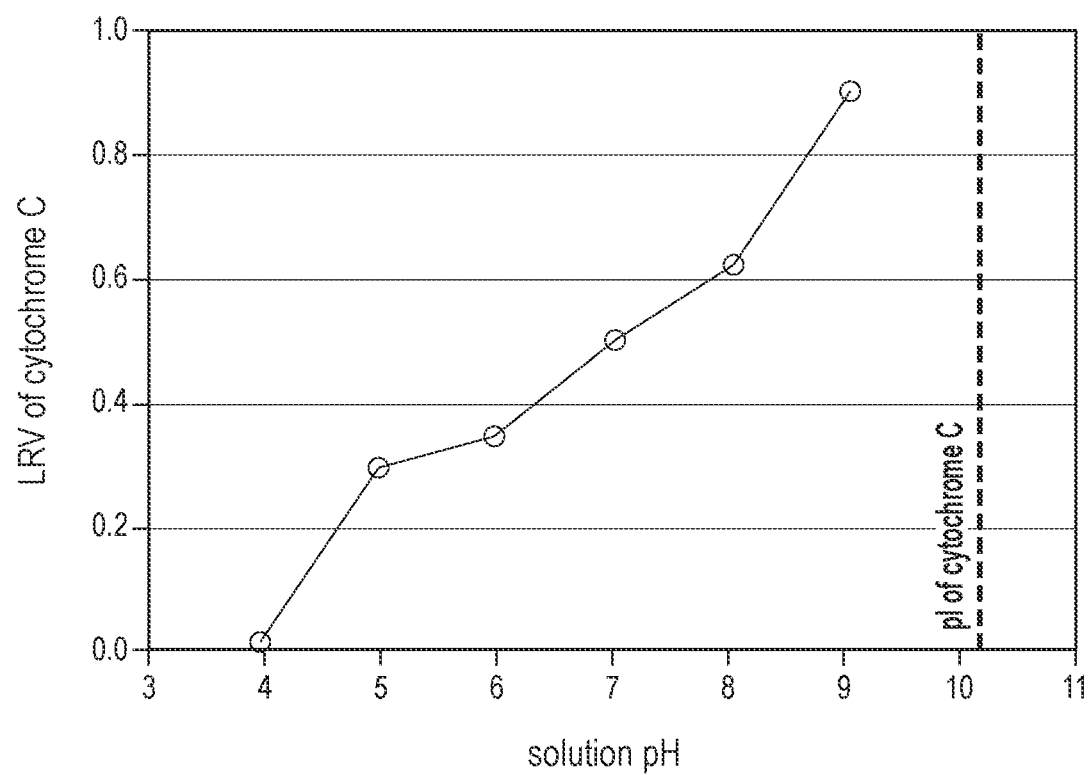
FIG. 2 is a graph depicting the results of a representative experiment to demonstrate the log reduction value (LRV) of cytochrome C removed from a mixture containing cytochrome C and a target protein (i.e., a monoclonal antibody (MAb I)) using activated carbon at pH 4.0, 5.0, 6.0, 7.0, 8.0 and 9.0 under static conditions. The mixture contained 5.0 mg/mL of MAb I and 1 mg/mL of cytochrome C (200,000 ppm). As depicted in FIG. 3, the optimal removal of cytochrome C using activated carbon is observed when the solution pH is closest to the isoelectric point of cytochrome C at pH 10.0-10.5. The X-axis depicts the solution pH and the Y-axis depicts the LRV of cytochrome C.

The Example demonstrates, as summarized in Table IV and FIG. 2, the unexpected finding that cytochrome C, which is an impurity in this case, is efficiently and selectively removed from the monoclonal antibody containing solution when the solution pH is near the isoelectric point of cytochrome C. Accordingly, when the solution was at pH 9.0, which is close to the isoelectric point of cytochrome C (i.e., pI 10.0-10.5), 0.9 LRV of the cytochrome C was removed. In contrast, only 0.01 LRV of the cytochrome C was removed by activated carbon at pH 4.0, which is further away from cytochrome C's isoelectric point.

The graph in FIG. 2 depicts the log reduction value (LRV) of cytochrome C removed from a monoclonal antibody (MAb 1) solution treated with activated carbon at pH 4.0, 5.0, 6.0, 7.0, 8.0, and 9.0 under static conditions. The greatest amount of cytochrome C is removed at pH 9.0 where the solution pH is closest to the cytochrome C's isoelectric point of 10.0-10.5. The graph exemplifies the unexpected finding that activated carbon most effectively removes a protein from a monoclonal antibody solution when the solution pH is near the isoelectric point of the protein to be removed.

Accordingly, this Example demonstrates the novel and unexpected finding that activated carbon can be used to remove a proteinaceous impurity from a solution containing a protein of interest by manipulating the solution pH such that it is close to the isoelectric point of the impurity.

TABLE IV

The recovery of monoclonal antibody MAb I, the concentration of cytochrome C, and the LRV of cytochrome C removed after solutions composed of 5.0 mg/mL MAb I and 1.0 mg/mL of cytochrome C (200,000 ppm) were treated with activated carbon at pH 4.0, 5.0, 6.0, 7.0, 8.0, or 9.0 under static conditions.

| pH | recovery of MAb I | cytochrome C concentration (ppm) | LRV of cytochrome C |
|---|---|---|---|
| 4 | >99% | 193,948 | 0.01 |
| 5 | 99% | 101,496 | 0.29 |
| 6 | 97% | 90,581 | 0.34 |
| 7 | 94% | 63,577 | 0.50 |
| 8 | 97% | 47,793 | 0.62 |
| 9 | >99% | 25,271 | 0.90 |

Example 5

Optimal Solution pH for the Removal of a Protein from a Solution Containing a Monoclonal Antibody This representative example demonstrates that an undesirable protein or model proteinaceous impurity can be selectively removed from a solution containing a monoclonal antibody as the target protein, using activated carbon, when the pH of the starting solution is brought close to the isoelectric point of the undesirable protein or proteinaceous impurity. In contrast to Example 4, the model impurity here is α-lactalbumin.

A solution containing a monoclonal antibody and 200,000 ppm α-lactalbumin was treated with activated carbon at pH 4.0, 5.0, 6.0, 7.0, 8.0 and 9.0 under static conditions to further demonstrate that activated carbon can be used for selective and efficient removal of yet another protein (i.e., α-lactalbumin) from a solution containing a protein of interest (i.e., a monoclonal antibody in this case) by manipulating the pH of the solution such that it is close to the isoelectric point of α-lactalbumin.

A 10.0 mg/mL solution of MAb I monoclonal antibody was dialyzed into water to remove buffer salts with dialysis tubing (Standard RC Dialysis Trial Kits, Spectra/Por® 1-3, 3.5K MWCO, 54 mm FLAT WIDTH, serial number: 132725, Spectrum Laboratories, Inc. Rancho Dominguez, Calif., 90220 USA). A portion of the dialyzed MAB I solution was then concentrated to using Amicon Ultra-15 Centrifugal Filter Units (3 kDa, catalogue Number: UFC900324. EMD Millipore Corporation, Billerica, Mass., 01821, USA). The concentrated portion of the solution was recombined with the rest of the dialyzed MAB 1 solution to give stock solution with a concentration of 10.0 mg/mL. The MAB I stock solution was then filtered through a 0.22 µm membrane (Stericup-GP 0.22 µm Millipore Express PLUS membrane, 250 mL, catalogue number: SCGPU02RE, EMD Millipore Corporation. Billerica, Mass., 01821, USA).

200 mg of α-lactalbumin from bovine milk (85% by PAGE, product number L5385, lot number 110M7003V, Sigma-Aldrich Corporation. St. Louis, Mo., 63103, USA) was dissolved into 100 mL of the 10.0 mg/mL MAB I solution. The stock solution was filtered through a 0.22 µm membrane (Stericup-GP 0.22 µm Millipore Express PLUS membrane, 250 mL, catalogue number: SCGPU02RE, EMD Millipore Corporation, Billerica, Mass., 01821, USA).

Three 15 mL centrifuge tubes for pH 4.0, 5.0, 6.0, 7.0, 8.0, and 9.0 were loaded with 10 mg of Nuchar HD activated carbon (MeadWestVaco Corporation. Richmond, Va., USA). Three separate 15 mL centrifuge tubes for each of pH values 4.0, 5.0, 6.0, 7.0, 8.0, and 9.0 were used as controls with no activated carbon. Subsequently, 2.5 mL of buffer at the appropriate pH (50 mM acetate for pH 4.0, 5.0, 6.0 or 50 mM Tris for pH 7.0, 8.0, 9.0) was added to each tube. 2.5 mL of the stock solution containing 10.0 mg/mL of MAB I and 2.0 mg/mL of α-lactalbumin was subsequently added to each tube. The resulting solutions had 5.0 mg/mL of MAB I, 1 mg/mL of α-lactalbumin, and a buffer concentration of 25 mM. The tubes were allowed to rotate for 20 hours.

The tubes were subjected to centrifugation and the supernatant solutions were filtered through a 0.22 micron membrane (Millex-GV 0.22 micron Filter Unit Durapore PVDF Membrane. EMD Millipore Corporation, Billerica, Mass., 01821, USA) in order to remove any activated carbon particles that might remain suspended in solution. The samples were analyzed by analytical size-exclusion chromatography (Instrument: Agilent 1260 HPLC; Column: Tosoh BiosciencesTSK-Gel Super SW3000; Mobile phase: 0.2M sodium phosphate pH 7.0; flow rate: (0.35 ml/min, isocratic gradient, 15 min run time; wavelength of UV detector: 230 nm; temperature: 25 degree C.). The recovery of each protein was calculated based on the A230 areas measured in the HPLC peaks.

Figure 3:
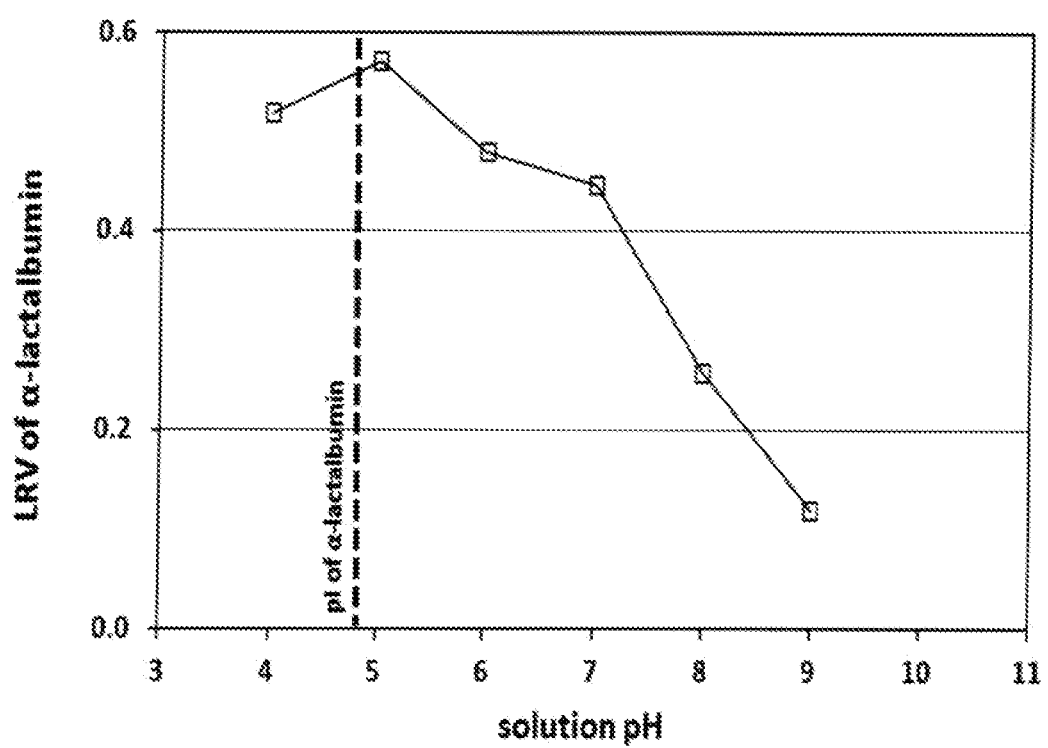
FIG. 3 is a graph depicting the results of a representative experiment to demonstrate the log reduction value (LRV) of α-lactalbumin removed from a mixture containing α-lactalbumin and a target protein (i.e., a monoclonal antibody (MAb I)) using activated carbon at pH 4.0, 5.0, 6.0, 7.0, 8.0 and 9.0 under static conditions. The mixture contained 5.0 mg/mL of MAb I and 1 mg/mL of α-lactalbumin (200,000 ppm). As depicted in FIG. 3, the optimal removal of α-lactalbumin using activated carbon is observed when the solution pH is closest to the isoelectric point of α-lactalbumin at 4.8. The X-axis depicts the solution pH and the Y-axis depicts the LRV of α-lactalbumin.

This example, summarized in Table V and FIG. 3, demonstrates, together with Example 4, that activated carbon can be used to selectively and efficiently remove practically any undesirable protein (α-lactalbumin in this case) present in a solution containing a protein of interest (a monoclonal antibody in this case), by simply adjusting the solution pH such that it is close to the isoelectric point of the undesirable protein. In this instance. α-lactalbumin was selectively and efficiently removed from the solution containing a monoclonal antibody, when the pH of the solution pH was near the isoelectric point of α-lactalbumin. For example, when the solution was at pH 5.0, which is near the isoelectric point of α-lactalbumin (pI 4.8), 0.57 LRV of the α-lactalbumin was removed. In contrast, only 0.12 LRV of the α-lactalbumin was removed by activated carbon at pH 9.0, which is further removed from much α-lactalbumin's isoelectric point.

The graph in FIG. 3 depicts the log reduction value (LRV) of α-lactalbumin removed from a monoclonal antibody (MAb I) solution treated with activated carbon at pH 4.0, 5.0, 6.0, 7.0, 8.0, and 9.0 under static conditions. As shown, the greatest amount of α-lactalbumin was removed at pH 5.0 where the solution pH is closest to the α-lactalbumin's isoelectric point of 4.8. The graph indicates the unexpected finding that activated carbon most effectively removes a protein from a monoclonal antibody solution when the solution pH is near the isoelectric point of the protein to be removed.

TABLE V

The recovery of monoclonal antibody MAb I, the concentration of α-lactalbumin, and the LRV of α-lactalbumin removed after solutions composed of 5.0 mg/mL MAb I and 1 mg/mL of α-lactalbumin (200,000 ppm) were treated with activated carbon at pH 4.0, 5.0, 6.0, 7.0, 8.0, or 9.0 under static conditions.

| pH | recovery of MAb I | α-lactalbumin concentration (ppm) | LRV of α-lactalbumin |
|---|---|---|---|
| 4 | >99% | 60,586 | 0.52 |
| 5 | >99% | 53,655 | 0.57 |
| 6 | 98% | 66,236 | 0.48 |
| 7 | 96% | 71,522 | 0.45 |
| 8 | 97% | 110,416 | 0.26 |
| 9 | 97% | 151,730 | 0.12 |

Example 6

Optimal Solution pH for the Removal of a Protein from a Mixture Containing a Monoclonal Antibody This representative example demonstrates that an undesirable protein or a model proteinaceous impurity can be selectively removed from a solution containing a monoclonal antibody as the target protein, using activated carbon, when the pH of the starting solution is brought to be close to the isoelectric point of the undesirable protein or proteinaceous impurity. In contrast to Examples 4 and 5, the model impurity here is lysozyme.

A solution containing MAb I monoclonal antibody and 200,000 ppm lysozyme was treated with activated carbon at pH 4.0, 5.0, 6.0, 7.0, 8.0 and 9.0 under static conditions to demonstrate that lysozyme can be selectively and efficiently removed from the solution using activated carbon when the solution pH is close to lysozyme's isoelectric point.

A 10.0 mg/mL solution of MAb I monoclonal antibody was dialyzed into water to remove buffer salts with dialysis tubing (Standard RC Dialysis Trial Kits. Spectra/Por® 1-3, 3.5K MWCO, 54 mm FLAT WIDTH, serial number: 132725, Spectrum Laboratories, Inc., Rancho Dominguez, Calif., 90220 USA). A portion of the dialyzed MAB I solution was then concentrated to using Amicon Ultra-15 Centrifugal Filter Units (3 kDa, catalogue Number: UFC900324, EMD Millipore Corporation, Billerica, Mass., 01821, USA). The concentrated portion of the solution was recombined with the rest of the dialyzed MAB I solution to give stock solution with a concentration of 10.0 mg/mL. The MAB I stock solution was then filtered through a 0.22 μm membrane (Stericup-GP 0.22 μm Millipore Express PLUS membrane, 250 mL, catalogue number: SCGPU02RE, EMD Millipore Corporation, Billerica, Mass., 01821, USA).

80 mg of Lysozyme from chicken egg white (≥98% SDS-PAGE, product number L4919, lot number 100M1897V1, Sigma-Aldrich Corporation St. Louis, Mo., 63103, USA) was dissolved into 40 mL of the 10.0 mg/mL MAB I solution. The stock solution was filtered through a 0.22 μm membrane (Stericup-GP 0.22 μm Millipore Express PLUS membrane, 250 mL, catalogue number: SCGPU02RE. EMD Millipore Corporation. Billerica, Mass., 01821, USA).

A centrifuge tube for pH 4.0, 5.0, 6.0, 7.0, 8.0, and 9.0 was loaded with 10 mg of Nuchar HD activated carbon (MeadWestVaco Corporation, Richmond, Va., USA). Separate 15 mL centrifuge tubes for pH 4.0, 5.0, 6.0, 7.0, 8.0, and 9.0 were used as controls with no activated carbon. 2.5 mL of buffer at the appropriate pH (50 mM acetate for pH 4.0, 5.0, 6.0 or 50 mM Tris for pH 7.0, 8.0, 9.0) was added to each tube. 2.5 mL of the stock solution containing 10.0 mg/mL of MAB I and 2 mg/mL of lysozyme was added to each tube. The resulting solutions had 5.0 mg/mL of MAB I, 1.0 mg/mL lysozyme, and a buffer concentration of 25 mM. The tubes were allowed to rotate for 20 hours.

The tubes were subsequently subjected to centrifugation and the supernatant solutions were filtered through a 0.22 micron membrane (Millex-GV 0.22 micron Filter Unit Durapore PVDF Membrane, EMD Millipore Corporation, Billerica, Mass., 01821, USA) in order to remove any activated carbon particles that might remain suspended in solution. The samples were analyzed by analytical size-exclusion chromatography (Instrument: Agilent 1260 HPLC; Column: Tosoh BiosciencesTSK-Gel Super SW3000; Mobile phase: 0.2M sodium phosphate pH 7.0; flow rate: 0.35 ml/min, isocratic gradient, 15 min run time; wavelength of UV detector: 230 nm; temperature: 25 degree C.). The recovery of each protein was calculated based on the A230 areas measured in the HPLC peaks.

Figure 4:
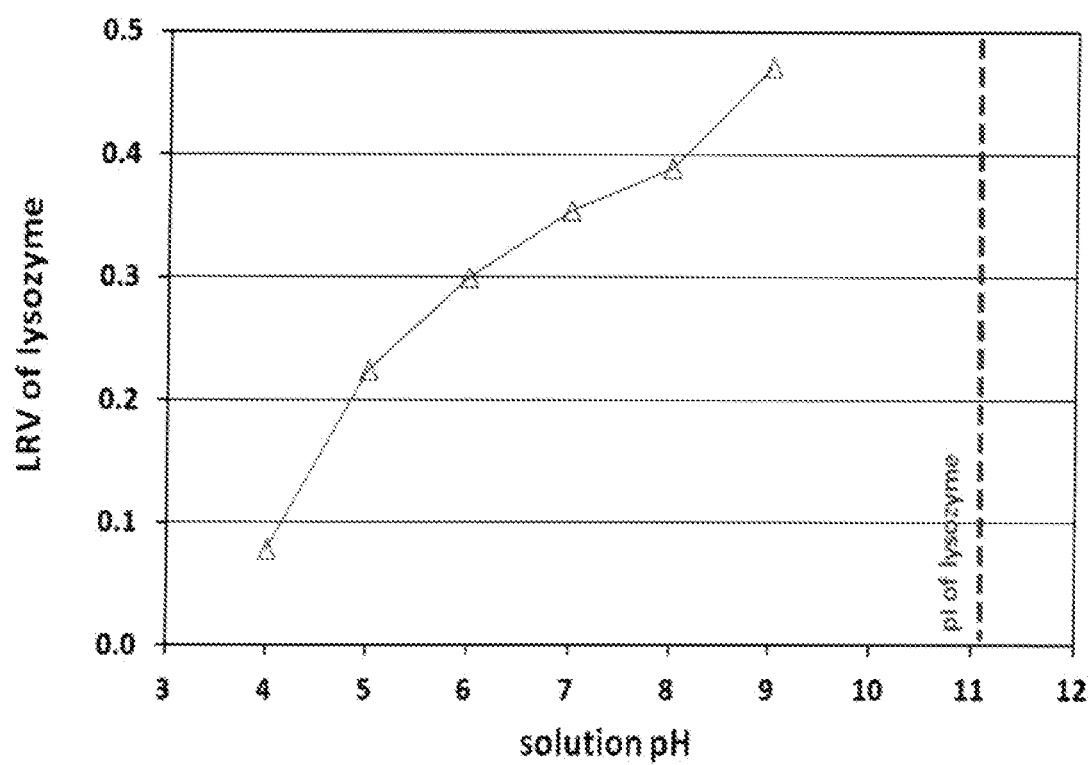
FIG. 4 is a graph depicting the results of a representative experiment to demonstrate the log reduction value (LRV) of lysozyme removed from a mixture containing lysozyme and a target protein (i.e., a monoclonal antibody (MAb I)) using activated carbon at pH 4.0, 5.0, 6.0, 7.0, 8.0 and 9.0 under static conditions. The solution contained 5.0 mg/mL MAb I and 1.0 mg/mL of lysozyme (200,000 ppm). As depicted in FIG. 4, the greatest amount of lysozyme is removed at pH 9.0 where the solution pH is closest to the lysozyme's isoelectric point of 11.2-11.3. The X-axis depicts the solution pH and the Y-axis depicts the LRV of lysozyme.

This Example demonstrates, as summarized in Table VI and FIG. 4, the unexpected finding that lysozyme, which is classified as an impurity in this case, is efficiently and selectively removed from the monoclonal antibody containing solution when the solution pH is near the isoelectric point of lysozyme. Accordingly, when the solution was at pH 9.0, which is close to the isoelectric point of lysozyme (i.e., pI 11.2-11.3), 0.47 LRV of the lysozyme was removed. In contrast, only 0.08 LRV of the lysozyme was removed by activated carbon at pH 4.0, which is further away from lysozyme's isoelectric point.

The graph in FIG. 4 shows the log reduction value (LRV) of lysozyme removed from a monoclonal antibody (MAb I) solution treated with activated carbon at pH 4.0, 5.0, 6.0, 7.0, 8.0, and 9.0 under static conditions. As shown, the greatest amount of lysozyme is removed at pH 9.0 where the solution pH is closest to the lysozyme's isoelectric point of 11.2-11.3. The graph demonstrates the unexpected finding that activated carbon most effectively removes a protein from a monoclonal antibody solution when the solution pH is near the isoelectric point of the protein to be removed.

Accordingly, this Example, together with Examples 4 and 5, demonstrates the novel and unexpected finding that activated carbon can be used to remove a proteinaceous impurity from a solution containing a protein of interest by manipulating the solution pH such that it is close to the isoelectric point of the impurity.

TABLE VI

The recovery of monoclonal antibody MAb I, the concentration of lysozyme, and the LRV of lysozyme removed after solutions composed of 5.0 mg/mL MAb I and 1.0 mg/mL of lysozyme (200,000 ppm) were treated with activated carbon at pH 4.0, 5.0, 6.0, 7.0, 8.0, or 9.0 under static conditions.

| pH | recovery of MAb I | lysozyme concentration (ppm) | LRV of lysozyme |
|---|---|---|---|
| 4 | >99% | 167,222 | 0.08 |
| 5 | 98% | 119,367 | 0.22 |

TABLE VI-continued

The recovery of monoclonal antibody MAb I, the concentration of lysozyme, and the LRV of lysozyme removed after solutions composed of 5.0 mg/mL MAb I and 1.0 mg/mL of lysozyme (200,000 ppm) were treated with activated carbon at pH 4.0, 5.0, 6.0, 7.0, 8.0, or 9.0 under static conditions.

| pH | recovery of MAb I | lysozyme concentration (ppm) | LRV of lysozyme |
|---|---|---|---|
| 6 | 97% | 100,302 | 0.30 |
| 7 | 96% | 88,381 | 0.35 |
| 8 | >99% | 81,721 | 0.39 |
| 9 | >99% | 67,555 | 0.47 |

Example 7

Optimal Solution pH for the Removal of a Protein from a Mixture Containing a Monoclonal Antibody This representative example demonstrates that a model proteinaceous impurity can be selectively removed from a solution containing a monoclonal antibody as the target protein, using activated carbon, when the pH of the starting solution is brought to be close to the isoelectric point of the proteinaceous impurity. In contrast to Examples 4, 5, and 6, the model impurity used in this example is BSA.

A solution containing MAb I monoclonal antibody and 100,000 ppm BSA was treated with activated carbon at pH 4.0, 5.0, 6.0, 7.0, 8.0 and 9.0 under static conditions to demonstrate that BSA can be selectively and efficiently removed from the solution using activated carbon when the solution pH is close to BSA's isoelectric point.

A 10.0 mg/mL solution of MAb I monoclonal antibody was dialyzed into water to remove buffer salts with dialysis tubing (Standard RC Dialysis Trial Kits, Spectra/Por® 1-3, 3.5K MWCO, 54 mm FLAT WIDTH, serial number: 132725, Spectrum Laboratories, Inc. Rancho Dominguez, Calif., 90220 USA). A portion of the dialyzed MAB I solution was then concentrated to using Amicon Ultra-15 Centrifugal Filter Units (3 kDa, catalogue Number: UFC900324, EMD Millipore Corporation, Billerica, Mass., 01821, USA). The concentrated portion of the solution was recombined with the rest of the dialyzed MAB I solution, resulting in a stock solution with a concentration of 10.0 mg/mL. The MAB I stock solution was then filtered through a 0.22 μm membrane (Stericup-GP 0.22 μm Millipore Express PLUS membrane, 250 mL, catalogue number: SCGPU02RE, EMD Millipore Corporation, Billerica, Mass., 01821, USA).

40 mg of Albumin from bovine serum (≥98% SDS-PAGE, product number A7906, lot number SLBC0647V, Sigma-Aldrich Corporation St. Louis, Mo., 63103, USA) was dissolved into 40 mL of the 10.0 mg/mL MAB I solution. The stock solution was filtered through a 0.22 μm membrane (Stericup-GP 0.22 μm Millipore Express PLUS membrane, 250 mL, catalogue number: SCGPU02RE, EMD Millipore Corporation, Billerica, Mass., 01821, USA).

A centrifuge tube for pH 4.0, 5.0, 6.0, 7.0, 8.0, and 9.0 was loaded with 10 mg of Nuchar HD) activated carbon (MeadWestVaco Corporation, Richmond, Va., USA). Separate 15 mL centrifuge tubes for pH 4.0, 5.0, 6.0, 7.0, 8.0, and 9.0 were used as controls with no activated carbon. 2.5 mL of buffer at the appropriate pH (50 mM acetate for pH 4.0, 5.0, 6.0 or 50 mM Tris for pH 7.0, 8.0, 9.0) was added to each tube. 2.5 mL of the stock solution containing 10.0 mg/mL of MAB I and 1 mg/mL of BSA was added to each tube. The resulting solutions had 5.0 mg/mL of MAB 1, 0.5 mg/mL of BSA, and a buffer concentration of 25 mM. The tubes were allowed to rotate for 20 hours.

The tubes were subsequently subjected to centrifugation and the supernatant solutions were filtered through a 0.22 micron membrane (Millex-GV 0.22 micron Filter Unit Durapore PVDF Membrane, EMD Millipore Corporation, Billerica, Mass., 01821, USA) in order to remove any activated carbon particles that might remain suspended in solution. The samples were analyzed by analytical size-exclusion chromatography (Instrument: Agilent 1260 HPLC; Column: Tosoh BiosciencesTSK-Gel Super SW3000; Mobile phase: 0.2M sodium phosphate pH 7.0; flow rate: 0.35 ml/min, isocratic gradient, 15 min run time; wavelength of UV detector: 230 nm; temperature: 25 degree C.). The recovery of each protein was calculated based on the A230 areas measured in the HPLC peaks.

Figure 5:
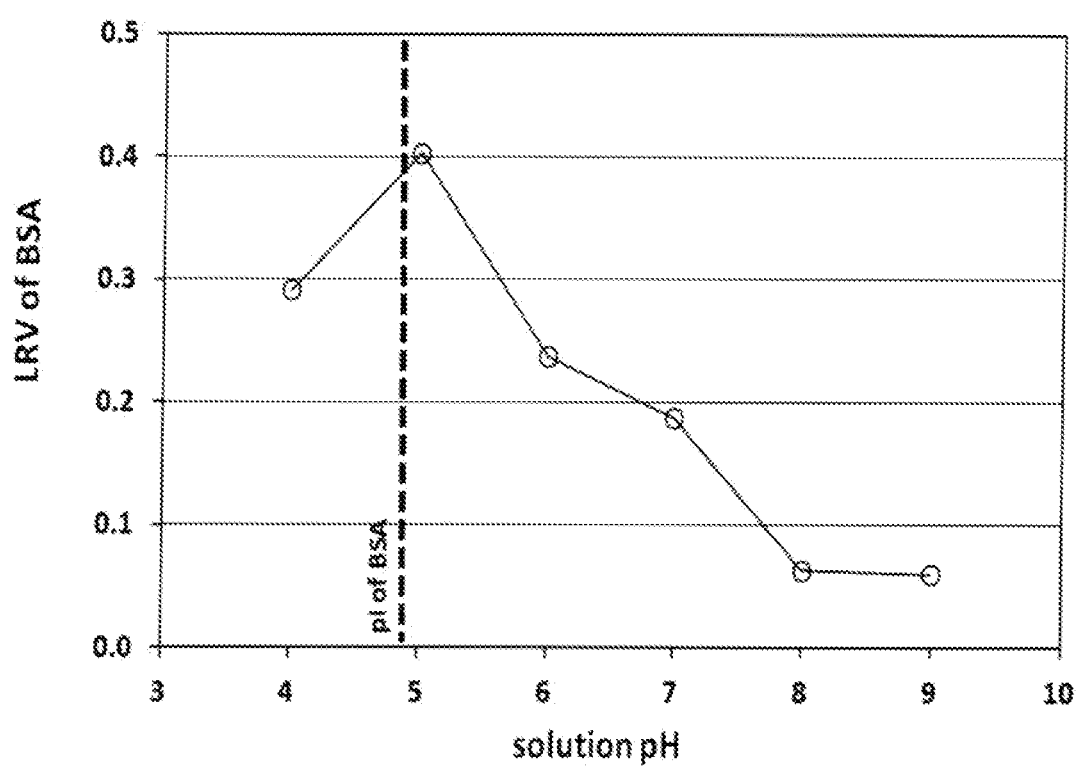
FIG. 5 is a graph depicting the results of a representative experiment to demonstrate the log reduction value (LRV) of BSA removed from a mixture containing BSA and a target protein (i.e., a monoclonal antibody (MAb 1)) using activated carbon at pH 4.0, 5.0, 6.0, 7.0, 8.0 and 9.0 under static conditions. The solution contained 5.0 mg/mL MAb I and 0.5 mg/mL of BSA (100,000 ppm). As depicted in FIG. 5, the greatest amount of BSA is removed at pH 5.0 where the solution pH is closest to the BSA's isoelectric point of 4.9. The X-axis depicts the solution pH and the Y-axis depicts the LRV of BSA.

This example demonstrates, as summarized in Table VII and FIG. 5, that BSA, which is used as a proteinaceous impurity in this case, is efficiently and selectively removed from the monoclonal antibody containing solution when the solution pH is near the isoelectric point of BSA. Accordingly, when the solution was at pH 5.0, which is close to the isoelectric point of BSA (i.e., pI 4.9), 0.40 LRV of the BSA was removed. In contrast, only 0.06 LRV of the BSA was removed by activated carbon at pH 9.0, which is further away from BSA's isoelectric point.

The graph in FIG. 5 depicts the log reduction value (LRV) of BSA removed from a monoclonal antibody (MAb I) solution treated with activated carbon at pH 4.0, 5.0, 6.0, 7.0, 8.0, and 9.0 under static conditions. As shown, the greatest amount of BSA was removed at pH 5.0 where the solution pH is closest to the BSA's isoelectric point of 4.9. The graph further supports the unexpected result that activated carbon most effectively removes a protein from a monoclonal antibody solution when the solution pH is near the isoelectric point of the protein to be removed.

Accordingly, this example, together with examples 4, 5, and 6 demonstrates the novel and unexpected finding that activated carbon can be used to remove a proteinaceous impurity from a solution containing a protein of interest by manipulating the solution pH such that it is close to the isoelectric point of the impurity.

TABLE VII

The recovery of monoclonal antibody MAb I, the concentration of BSA, and the LRV of BSA removed after solutions composed of 5.0 mg/mL MAb I and 0.5 mg/mL of BSA (100,000 ppm) were treated with activated carbon at pH 4.0, 5.0, 6.0, 7.0, 8.0, or 9.0 under static conditions.

| pH | recovery of MAb I | BSA concentration (ppm) | LRV of BSA |
|---|---|---|---|
| 4 | >99% | 51,105 | 0.29 |
| 5 | 99% | 39,565 | 0.40 |
| 6 | 99% | 57,960 | 0.24 |
| 7 | >99% | 65,014 | 0.19 |
| 8 | 99% | 86,505 | 0.06 |
| 9 | 99% | 87,149 | 0.06 |

Example 8

Selective Removal of Cytochrome C Protein from a Solution of α-Lactalbumin Using Several Different Types of Activated Carbon This representative example demonstrates that the methods described herein can be successfully carried out using several different types of activated carbon.

A solution of α-lactalbumin with 100,000 ppm of cytochrome C, used as a model proteinaceous impurity, was treated with several different types of activated carbon at pH 4.0 and pH 9.0. This example demonstrates that several different types of activated carbon can be used to selectively and efficiently remove a proteinaceous impurity from a sample containing a target protein by choosing a solution pH close to the isoelectric point of the proteinaceous impurity.

A solution was prepared using 800 mg of α-lactalbumin from bovine milk (≥85% by PAGE, product number L5385, lot number 110M7003V, Sigma-Aldrich Corporation, St. Louis, Mo., 63103, USA), 80 mg of cytochrome C from equine heart (≥95% by SDS-PAGE, product number C2506, lot number 84117135 Sigma-Aldrich Corporation. St. Louis, Mo., 63103, USA) and 80 mL of water. The protein stock solution consisting of 10.0 mg/mL of α-lactalbumin and 1.0 mg/mL of cytochrome C in water was then filtered through a 0.22 μm membrane (Stericup-GP 0.22 μm Millipore Express PLUS membrane, 250 mL, catalogue number: SCGPU02RE, EMD Millipore Corporation, Billerica, Mass., 01821, USA).

Three 15 mL centrifuge tubes at both pH 4.0 and pH 9.0 were loaded with either 10 mg of MeadWestVaco Nuchar HD activated carbon (MeadWestVaco Corporation, Richmond, Va., USA), 10 mg of Norit Darko KB-G activated carbon (Norit Americas Inc., Marshall, Tex., USA), or 10 mg of Norit CGP Super activated carbon (Norit Americas Inc., Marshall, Tex., USA). Three separate 15 mL centrifuge tubes at pH 4.0 and pH 9.0 were used as controls with no activated carbon. 2.5 mL of buffer at the appropriate pH (50 mM acetate for pH 4.0, 50 mM Tris for pH 9.0) was added to each tube. 2.5 mL of the stock protein solution having 10.0 mg/mL of α-lactalbumin and 1.0 mg/mL of cytochrome C in water was subsequently added to each tube. This gave a solution with 5.0 mg/mL of α-lactalbumin, 0.5 mg/mL of cytochrome C, and a buffer concentration of 25 mM. The tubes were allowed to rotate for 20 hours.

The tubes were subsequently subjected to centrifugation and the supernatant solutions were filtered through a 0.22 micron membrane (Millex-GV 0.22 micron Filter Unit Durapore PVDF Membrane, EMD Millipore Corporation, Billerica, Mass., 01821, USA) in order to remove any activated carbon particles that might remain suspended in solution. The samples were analyzed by reverse phase HPLC (Instrument: Agilent 1290 UPLC. Column: Higgins Analytical Targa C18, Mobile phase: Solvent A—0.1% trifluoroacetic acid in MilliQ Water, Solvent B—0.1% trifluoroacetic acid in 100% acetonitrile (HPLC grade), flow rate: 1 ml/min, gradient: 0-15 min, 5%-95% B, with 10 minute post-time to re-equilibrate column, wavelength of UV detector: 230 nm (550 nm reference, temperature: 25° C.). The recovery of the proteins was calculated based on the areas measured in the HPLC peaks.

This example demonstrates as summarized in Table VIII that cytochrome C, used as a model impurity herein, can be selectively and efficiently removed from the solution containing α-lactalbumin at pH 9.0, which is near the isoelectric point of cytochrome C (pI 10.0-10.5) using three different types of activated carbon tested. In contrast, very little of the cytochrome C impurity is removed from the α-lactalbumin solution at pH 4.0, which is much further away from the isoelectric point of cytochrome C in case of all three types of the activated carbons tested. Accordingly, this example demonstrates that the ability of activated carbon to remove protein impurities is not limited to a specific type of activated carbon, but applies generally to a variety of different activated carbon types.

TABLE VIII

The concentration of cytochrome C relative to α-lactalbumin in ppm remaining in solution after treatment with several different types of activated carbon at pH 4.0 and pH 9.0.

| type of activated carbon | concentration of cytochrome C (ppm) | |
|---|---|---|
| | pH 4.0 | pH 9.0 |
| control (no activated carbon) | 100,000 | 100,000 |
| MeadWestvaco Nuchar HD | 87,247 | 0 |
| Norit Darko KB-G | 92,211 | 0 |
| Norit CGP Super | 92,766 | 0 |

Example 9

Selective Removal of Cytochrome C Protein from a Solution of α-Lactalbumin Flowed Through a Packed Column of Activated Carbon This representative example demonstrates that the methods described herein can be carried out in a flow-through dynamic mode using activated carbon packed into a device. As demonstrated herein, activated carbon can be used to selectively and efficiently remove an undesirable protein or proteinaceous impurity from a sample containing a target protein by choosing a solution pH close to the isoelectric point of the undesirable protein or proteinaceous impurity under dynamic flow-through conditions.

A solution was prepared using 1500 mg of α-lactalbumin from bovine milk (≥85% by PAGE, product number L5385, lot number 110M7003V, Sigma-Aldrich Corporation, St. Louis, Mo., 63103, USA), 150 mg of cytochrome C from equine heart (≥95% by SDS-PAGE, product number C2506, lot number 84H7135 Sigma-Aldrich Corporation, St. Louis, Mo., 63103, USA) and 150 mL of water. The protein stock solution consisting of 10.0 mg/mL of α-lactalbumin and 1.0 mg/mL of cytochrome C in water was then filtered through a 0.22 μm membrane (Stericup-GP 0.22 μm Millipore Express PLUS membrane, 250 mL, catalogue number: SCGPU02RE, EMD Millipore Corporation. Billerica, Mass., 01821, USA).

The stock solution at pH 4.0 was prepared by mixing a 60 mL portion of the stock solution in water with 60 mL of 50 mM sodium acetate at pH 4.0 to give a solution with 5.0 mg/mL of α-lactalbumin, 0.5 mg/mL of cytochrome C, and 25 mM acetate at pH 4.0. The stock solution at pH 9.0 was prepared by mixing a 60 mL portion of the stock solution in water with 60 mL of 50 mM Tris at pH 9.0 to give a solution with 5.0 mg/mL of α-lactalbumin, 0.5 mg/mL of cytochrome C, and 25 mM Tris at pH 9.0. The stock solutions were then filtered through a 0.22 μm membrane (Stericup-GP 0.22 am Millipore Express PLUS membrane, 250 mL, catalogue number: SCGPU02RE, EMD Millipore Corporation. Billerica, Mass., 01821, USA).

Two glass chromatography columns (Omnifit Benchmark Column 10 mm/100 mm, 10 mm diameter, 100 mm length, SKU: 006BCC-10-10-AF, Diba Industries, Danbury, Conn. 06810, US) were loaded with 200 mg of Nuchar HD activated carbon (MeadWestVaco Corporation, Richmond, Va., USA) slurried in water to give a packed column volume of 0.8 mL. The columns were packed by flowing an aqueous buffer through the activated carbon slurry. One column was equilibrated with 25 mM sodium acetate at pH 4.0 and the second was equilibrated with 25 mM Tris at pH 9.0.

100 mL of the stock solutions at pH 4.0 or pH 9.0 were passed through the appropriately equilibrated activated carbon columns at 0.4 ml/min, resulting in a residence time of 2.0 mitts in the activated carbon column followed by 12.5 mL of buffer (25 mM sodium acetate at pH 4.0, 25 mM Tris at pH 9.0). Nine fractions of 12.5 mL were collected. The individual fractions and a pooled sample of all nine were submitted for reverse phase HPLC analysis. The samples were analyzed by reverse phase HPLC (Instrument: Agilent 1290 UPLC, Column: Higgins Analytical Targa C18, Mobile phase: Solvent A—0.1% trifluoroacetic acid in MilliQ Water, Solvent B—0.1% trifluoroacetic acid in 100% acetonitrile (HPLC grade), flow rate: 1 ml/min, gradient: 0-15 min. 5%-95% B, with 10 minute post-time to re-equilibrate column, wavelength of UV detector: 230 nm (550 nm reference, temperature: 25° C.). The recovery of the proteins was calculated based on the areas measured in the HPLC peaks.

Figure 6:
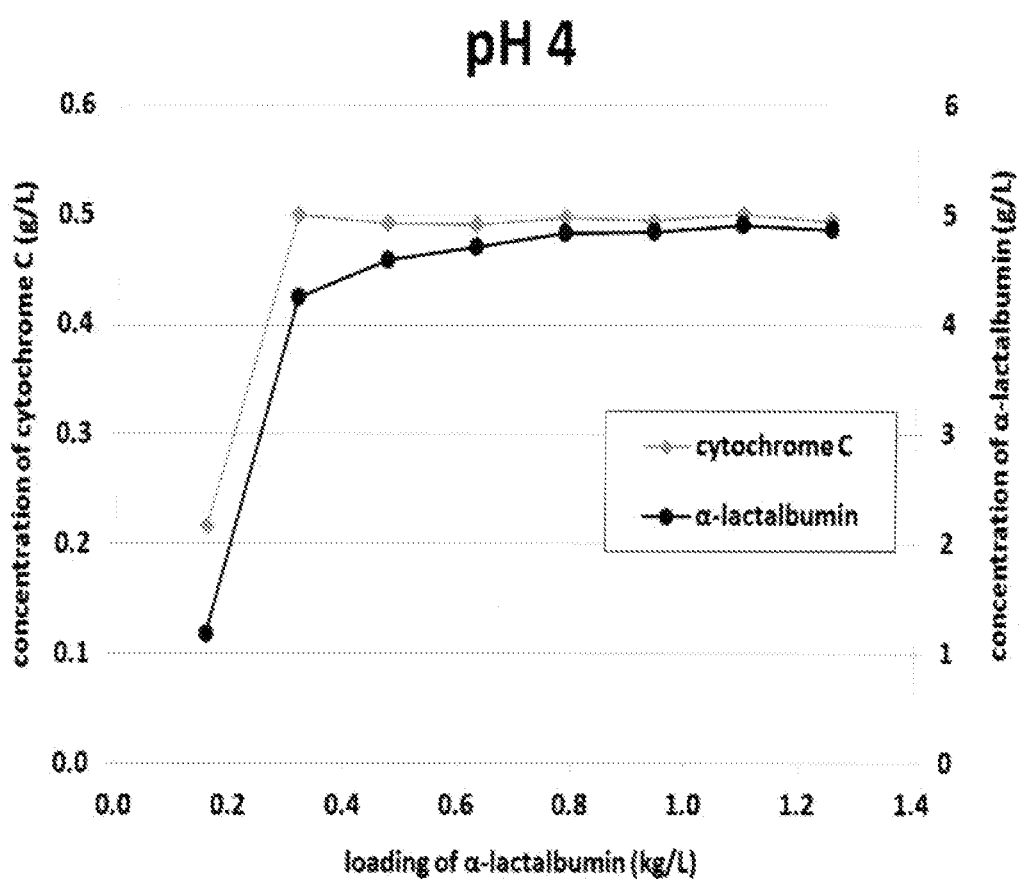
FIG. 6 is a graph depicting the results of a representative experiment to demonstrate that an undesirable protein is not efficiently removed when it is flowed through activated carbon at a solution pH that is far removed from the isoelectric point of the undesirable protein. The graph shows the concentration of cytochrome C and α-lactalbumin in 12.5 mL fractions that were collected after a solution of 5.0 mg/mL of α-lactalbumin and 0.5 mg/mL of cytochrome C at pH 4.0 was passed through a column of activated carbon. Both the lower concentration cytochrome C and the higher concentration α-lactalbumin were eluted off the column at about the same ratio that they entered the column.
Figure 7:
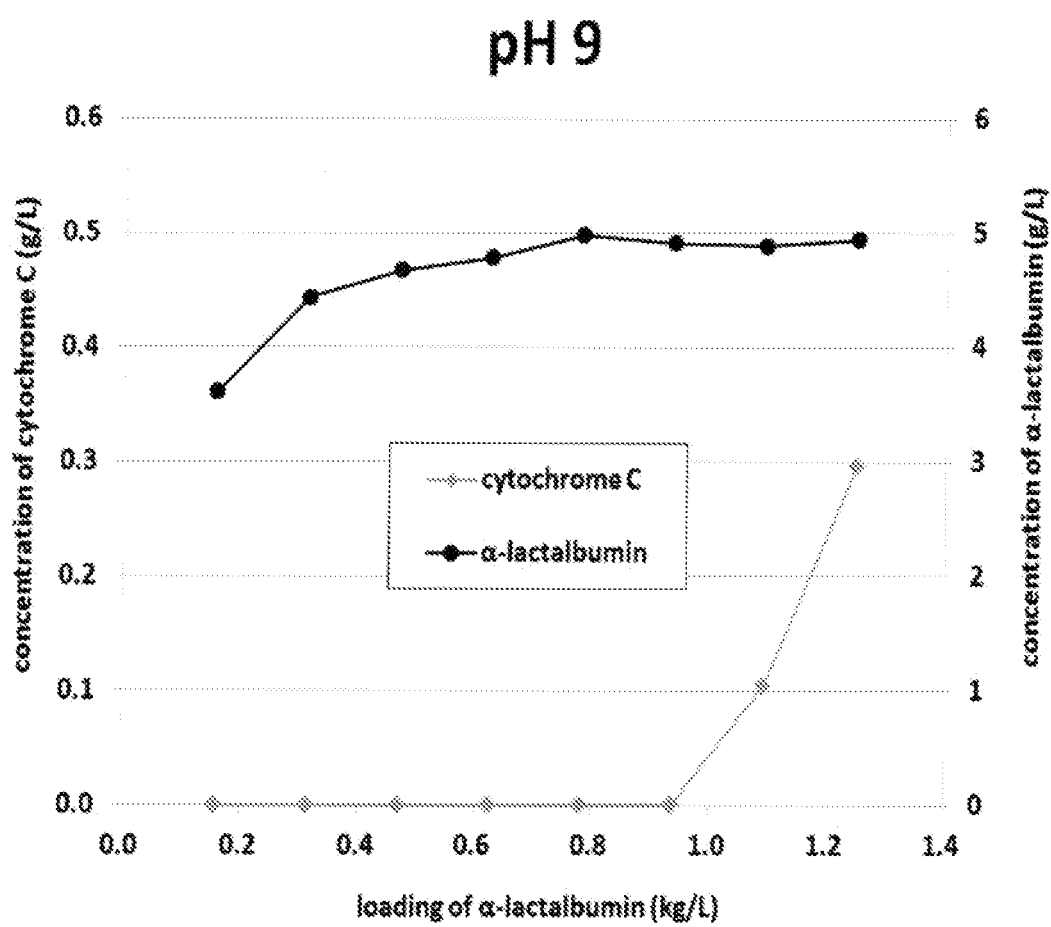
FIG. 7 is a graph depicting the results of a representative experiment to demonstrate that an undesirable protein is very efficiently removed when it is flowed through activated carbon at a solution pH that is close to isoelectric point of the undesirable protein. The graph shows the concentration of cytochrome C and α-lactalbumin in 12.5 mL fractions that were collected after a solution of 5.0 mg/mL of α-lactalbumin and 0.5 mg/mL of cytochrome C at pH 9.0 was passed through a column of activated carbon. Cytochrome C did not break through the column until it had been loaded with 1.09 kg of α-lactalbumin per liter of activated carbon. As demonstrated in FIG. 7, activated carbon provided excellent removal of the cytochrome C from the solution of α-lactalbumin at pH 9.0, which is close to cytochrome C's isoelectric point of pH 10.0-10.5. The X-axis depicts the loading of α-lactalbumin in kg/L; the left Y-axis depicts the concentration of cytochrome C in g/L and the right Y-axis depicts the concentration of α-lactalbumin in g/L.

The results of this example demonstrate, as summarized in Table IX and Table X as well as FIGS. 6 and 7, that activated carbon can be used to selectively and efficiently remove an undesirable protein or proteinaceous impurity from a sample containing a target protein by choosing a solution pH close to the isoelectric point of the undesirable protein or proteinaceous impurity under flow conditions. The flow-through removal of cytochrome C, used as a model proteinaceous impurity in this example, from a solution containing α-lactalbumin using activated carbon was highly dependent on solution pH. At pH 4.0 the cytochrome C broke through in the very first fraction along with α-lactalbumin. In contrast, at pH 9.0, the breakthrough of cytochrome C was not observed until the seventh fraction when the column had been loaded with 1.09 kg of α-lactalbumin per L of activated carbon. The overall recovery of α-lactalbumin calculated from a pool of the individual fractions was only 88% at pH 4.0 while it was 94% at pH 9.0. After the solution was passed through the activated carbon column at pH 4.0, the concentration of cytochrome C relative to α-lactalbumin was increased from 100.000 ppm to 106,125 ppm resulting in a LRV of cytochrome C of −0.03. In contrast, after the solution was passed through the activated carbon column at pH 9.0, the concentration of cytochrome C relative to α-lactalbumin was significantly decreased from 100.000 ppm to 10,584 ppm resulting in a LRV of cytochrome C of 0.98. This example demonstrates that the ideal solution pH for increasing the purity of a target protein in a sample using activated carbon under flow conditions is at a solution pH near the isoelectric point of the proteinaceous impurity or undesirable protein to be removed from the sample.

FIG. 6 depicts the concentration of cytochrome C and α-lactalbumin in 12.5 mL fractions that were collected after a solution of 5.0 mg/mL of α-lactalbumin and 0.5 mg/mL of cytochrome C at pH 4 was passed through a column of activated carbon. The graph demonstrates that the removal of cytochrome C from α-lactalbumin by treatment with activated carbon under flow conditions is ineffective because the solution pH of 4.0 is further from the 10.0-10.5 isoelectric point of cytochrome C.

FIG. 7 depicts the concentration of cytochrome C and α-lactalbumin in 12.5 mL fractions that were collected after a solution of 5.0 mg/mL of α-lactalbumin and 0.5 mg/mL of cytochrome C at pH 9 was passed through a column of activated carbon. The graph demonstrates that the removal of cytochrome C from α-lactalbumin by treatment with activated carbon under flow conditions is effective because the solution pH of 9.0 is close to the 10.0-10.5 isoelectric point of cytochrome C.

TABLE IX

Concentration of cytochrome C and α-lactalbumin in mg/mL for column fractions collected, after a solution containing 0.5 mg/mL cytochrome C and 5 mg/mL α-lactalbumin was flowed through a column of activated carbon at pH 4.0 or pH 9.0.

| α-lactalbumin loading on activated carbon (kg/L) | purification at pH 4.0 | | purification at pH 9.0 | |
|---|---|---|---|---|
| | cytochrome C concentration (mg/mL) | α-lactalbumin concentration (mg/mL) | cytochrome C concentration (mg/mL) | α-lactalbumin concentration (mg/mL) |
| 0.16 | 0.22 | 1.18 | 0.00 | 3.61 |
| 0.31 | 0.50 | 4.25 | 0.00 | 4.44 |
| 0.47 | 0.49 | 4.59 | 0.00 | 4.67 |
| 0.63 | 0.49 | 4.71 | 0.00 | 4.79 |
| 0.78 | 0.50 | 4.84 | 0.00 | 4.98 |
| 0.94 | 0.49 | 4.85 | 0.00 | 4.92 |
| 1.09 | 0.50 | 4.91 | 0.10 | 4.89 |
| 1.23 | 0.49 | 4.87 | 0.30 | 4.95 |

TABLE X

Concentration of cytochrome C relative to α-lactalbumin in ppm for column fractions collected, after a solution containing 100,000 ppm cytochrome C in 5 mg/mL of α-lactalbumin was flowed through a column of activated carbon at pH 4.0 or pH 9.0.

| loading of α-lactalbumin on activated carbon for fraction (kg/L) | pH 4.0 - cytochrome C concentration (ppm) | pH 9.0 - cytochrome C concentration (ppm) |
|---|---|---|
| 0.16 | 182,806 | 0 |
| 0.31 | 117,412 | 0 |
| 0.47 | 107,121 | 0 |
| 0.63 | 104,286 | 0 |

TABLE X-continued

Concentration of cytochrome C relative to α-lactalbumin in ppm for column fractions collected, after a solution containing 100,000 ppm cytochrome C in 5 mg/mL of α-lactalbumin was flowed through a column of activated carbon at pH 4.0 or pH 9.0.

| loading of α-lactalbumin on activated carbon for fraction (kg/L) | pH 4.0 - cytochrome C concentration (ppm) | pH 9.0 - cytochrome C concentration (ppm) |
| --- | --- | --- |
| 0.78 | 102,813 | 0 |
| 0.94 | 102,109 | 0 |
| 1.09 | 101,941 | 21,391 |
| 1.25 | 101,477 | 59,940 |

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of selectively removing a proteinaceous impurity from a sample comprising at least an immunoglobulin and the proteinaceous impurity, the method comprising the steps of:
   (a) providing a sample comprising at least an immunoglobulin and a proteinaceous impurity;
   (b) adjusting the solution pH of the sample, such that the pH is within 2.0 pH units of the isoelectric point of the proteinaceous impurity to be selectively removed;
   (c) contacting the sample with activated carbon, wherein the activated carbon selectively binds the proteinaceous impurity to be selectively removed; and
   (d) removing the activated carbon from the sample,
   thereby resulting in selective-removal of the activated carbon bound proteinaceous impurity from the sample and an increase in the concentration of the immunoglobulin to the proteinaceous impurity in the sample of 70% or more when measured.

2. The method of claim 1, wherein the pH is within 1.0 pH unit of the isoelectric point of the proteinaceous impurity to be selectively removed.

3. The method of claim 1, wherein the immunoglobulin is a monoclonal antibody.

4. The method of claim 1, wherein the immunoglobulin is a polyclonal antibody.

5. The method of claim 1, wherein the removing step comprises filtration or centrifugation.

6. The method of claim 1, wherein the immunoglobulin is a recombinant immunoglobulin.

7. The method of claim 1, wherein the sample comprises a cell culture feed.

8. The method of claim 7, wherein the cell culture feed is a CHO cell culture feed.

9. The method of claim 1, wherein the immunoglobulin is expressed in a mammalian expression system.

10. The method of claim 1, wherein the immunoglobulin is expressed in a non-mammalian expression system.

11. The method of claim 1, wherein the sample is subjected to a clarification step prior to the adjusting step.

12. The method of claim 11, wherein the clarification step is selected from the group consisting of centrifugation, settling, depth or screen filtration, complexing with flocculants, and pH change.

13. The method of claim 1, wherein the increase in the concentration of the immunoglobulin to the proteinaceous impurity in the sample is 80% or more.

14. The method of claim 1, wherein the increase in the concentration of the immunoglobulin to the proteinaceous impurity in the sample is 90% or more.

15. The method of claim 1, the method further comprising a sample with multiple impurities and, between steps a) and b), determining the isoelectric focusing point or points of the multiple impurities in the sample and identifying which proteinaceous impurity or impurities are to be selectively removed from the sample.

16. The method of claim 15, wherein said isoelectric point or points is determined by focusing electrophoresis gel, capillary isoelectric focusing or two-dimensional gel electrophoresis.

* * * * *